United States Patent
Jonckers et al.

(10) Patent No.: US 8,399,429 B2
(45) Date of Patent: Mar. 19, 2013

(54) URACYL CYCLOPROPYL NUCLEOTIDES

(75) Inventors: Tim Hugo Maria Jonckers, Edegem (BE); Pierre Jean-Marie Bernard Raboisson, Rosieres (BE); Steven Maurice Paula Van Hoof, Merelbeke (BE); Leen Anna Maria Vandekerckhove, Waregem (BE); Koen Vandyck, Paal-Beringen (BE)

(73) Assignees: Janssen Products, LP, Horsham, PA (US); Medivir AB, Huddinge (SE)

( * ) Notice: Subject to any disclaimer, the term of this patent is extended or adjusted under 35 U.S.C. 154(b) by 114 days.

(21) Appl. No.: 13/130,602

(22) PCT Filed: Dec. 8, 2009

(86) PCT No.: PCT/EP2009/066562
§ 371 (c)(1),
(2), (4) Date: May 23, 2011

(87) PCT Pub. No.: WO2010/066699
PCT Pub. Date: Jun. 17, 2010

(65) Prior Publication Data
US 2011/0230436 A1     Sep. 22, 2011

(30) Foreign Application Priority Data
Dec. 8, 2008   (EP) ................... 08171006

(51) Int. Cl.
*A01N 43/04*   (2006.01)
*A61K 31/70*   (2006.01)

(52) U.S. Cl. ........... 514/51; 514/43; 514/49; 514/50; 536/28.1; 536/28.4; 536/28.53; 536/28.55

(58) Field of Classification Search .............. None
See application file for complete search history.

(56) References Cited

FOREIGN PATENT DOCUMENTS

| | | |
|---|---|---|
| WO | WO 94/14436 A1 | 7/1994 |
| WO | WO 2004/002999 A2 | 1/2004 |
| WO | WO 2008/043704 A1 | 4/2008 |

OTHER PUBLICATIONS

Krieger, "Enhancement of Hepatitis C Virus RNA Replication by Cell Culture-Adaptive Mutations", Journal of Virology, vol. 75, pp. 4614-4624 (2001).
Lohmann et al., "Replication of Subgenomic Hepatitis C Virus RNAs in a Hepatoma Cell Line", Science, vol. 285, pp. 110-113 (1999).
Samano, "Synthesis and Radical-Induced Ring-Opening Reactions of 2'-Deoxyadenosine-2' Spirocyclopropane and Its Uridine Analogue. Mechanistic Probes for Ribonucleotide Reductases", Journal of American Chemical Society, vol. 114, pp. 4007-4008. (1992).

*Primary Examiner* — Patrick Lewis
(74) *Attorney, Agent, or Firm* — Andrea Jo Kamage

(57) ABSTRACT

Compounds of the formula I:

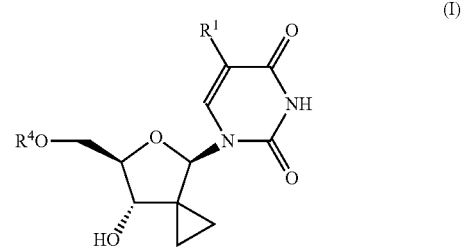

including any possible stereoisomers thereof, wherein:
$R^1$ is hydrogen or halo;
$R^4$ is a monophosphate, diphosphate or triphosphate ester; or $R^4$ is a group of formula

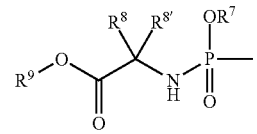

$R^7$ is optionally substituted phenyl; naphthyl; indolyl or N—$C_1$-$C_6$alkyloxycarbonyl-indolyl;
$R^8$ is hydrogen, $C_1$-$C_6$alkyl, benzyl;
$R^{8'}$ is hydrogen, $C_1$-$C_6$alkyl, benzyl; or
$R^8$ and $R^{8'}$ together with the carbon atom to which they are attached form $C_3$-$C_7$cycloalkyl;
$R^9$ is $C_1$-$C_{10}$alkyl, benzyl, or optionally substituted phenyl; or a pharmaceutically acceptable salt or solvate thereof.
pharmaceutical formulations and the use of compounds I as HCV inhibitors.

15 Claims, No Drawings

URACYL CYCLOPROPYL NUCLEOTIDES

This application is a national stage application of PCT/EP2009/066562, filed Dec. 8, 2009, which claims priority benefit of Application No. EP 08171006.3 filed Dec. 8, 2008. The complete disclosures of the aforementioned related patent applications are hereby incorporated herein by reference for all purposes.

TECHNICAL FIELD

This invention relates to novel nucleotides, which are inhibitors of the polymerase of hepatitis C virus (HCV) and their use in the treatment or prophylaxis of HCV.

BACKGROUND OF THE INVENTION

HCV is a single stranded, positive-sense RNA virus belonging to the Flaviviridae family of viruses in the hepacivirus genus. The NS5B region of the RNA polygene encodes a RNA dependent RNA polymerase (RdRp), which is essential to viral replication. Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations.

There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 HCV and about 80% of those infected by genotypes 2 and 3. Beside the limited efficacy on HCV genotype 1, this combination therapy has significant side effects and is poorly tolerated in many patients. Major side effects include influenza-like symptoms, hematologic abnormalities, and neuropsychiatric symptoms. Hence there is a need for more effective, convenient and better-tolerated treatments.

Experience with HIV drugs, in particular with HIV protease inhibitors, has taught that sub-optimal pharmacokinetics and complex dosing schemes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design.

The NS5B RdRp is essential for replication of the single-stranded, positive sense, HCV RNA genome. This enzyme has elicited significant interest among medicinal chemists. Both nucleoside and non-nucleoside inhibitors of NS5B are known. Nucleoside inhibitors can act as well as a chain terminator or as a competitive inhibitor, which interferes with nucleotide binding to the polymerase. To function as a chain terminator the nucleoside analog has to be taken up by the cell and converted in vivo to a triphosphate. This conversion to the triphosphate is commonly mediated by cellular kinases which imparts additional structural requirements on a potential nucleoside polymerase inhibitor. In addition this limits the direct evaluation of nucleosides as inhibitors of HCV replication to cell-based assays capable of in situ phosphorylation.

Several attempts have been made to develop nucleosides as inhibitors of HCV RdRp, but while a handful of compounds have entered clinical development, none have proceeded all the way to registration. Amongst the problems which HCV targeted nucleosides to date have encountered are toxicity, mutagenicity, lack of selectivity, poor efficacy, poor bioavailability, sub-optimal dosage regimes and ensuing high pill burden, and cost of goods.

Several patents and patent applications as well as scientific publications discloses nucleoside analogs having HCV inhibitory activity. WO 2004/002999 discloses modified 2' and 3'-nucleoside prodrugs for treating flaviridae infections. WO 2008/043704 discloses 4-amino-1-((2R,3 S,4S,5R)-5-azido-4-hydroxy-5-hydroxymethyl-3-methyl-tetrahydrofuran-2-yl)-1H-pyrimidin-2-one and ester derivatives as HCV polymerase inhibitors.

There is a need for HCV inhibitors that may overcome the disadvantages of current HCV therapy such as side effects, limited efficacy, the emerging of resistance, and compliance failures, as well as improve the sustained viral response.

The present invention concerns a group of HCV inhibiting 1-(7-hydroxy-6-hydroxymethyl-5-oxa-spiro[2.4]hept-4-yl)-1H,3H-pyrimidin-2,4-dione derivatives with useful properties regarding one or more of the following parameters: antiviral efficacy, favorable profile of resistance development, lack of toxicity and genotoxicity, favorable pharmacokinetics and pharmacodynamics and ease of formulation and administration. The compound 1-((4R,6R,7S)-7-hydroxy-6-hydroxymethyl-5-oxa-spiro[2.4]hept-4-yl)-1H,3H-pyrimidin-2,4-dione, also referred to as 2'-deoxy-2'-spirocyclopropyluridine has been described in J. Am, Chem. Soc., 1992, 114, 4007-4008.

Compounds of the invention may also be attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

DESCRIPTION OF THE INVENTION

In one aspect the present invention provides compounds, which can be represented by the formula I:

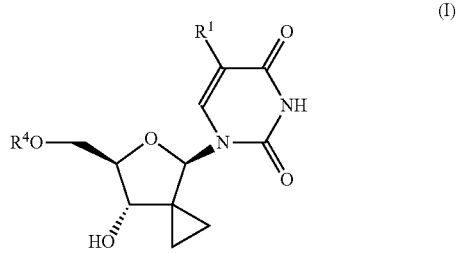

including any possible stereoisomers thereof, wherein:
$R^1$ is hydrogen or halo;
$R^4$ is a monophosphate, diphosphate or triphosphate ester; or $R^4$ is a group of formula

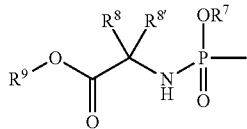

$R^7$ is phenyl, optionally substituted with 1, 2, or with 3 substituents each independently selected from halo, $C_1$-$C_6$alkyl, $C_3$-$C_6$alkenyl, $C_1$-$C_6$alkoxy, $C_1$-$C_6$alkoxycarbonyl, hydroxy, and amino; or $R^7$ is naphthyl; or $R^7$ is indolyl or N—$C_1$-$C_6$alkyloxycarbonylindolyl;
$R^8$ is hydrogen, $C_1$-$C_6$alkyl, benzyl;
$R^{8'}$ is hydrogen, $C_1$-$C_6$alkyl, benzyl; or
$R^8$ and $R^{8'}$ together with the carbon atom to which they are attached form $C_3$-$C_7$cycloalkyl;
$R^9$ is $C_1$-$C_{10}$alkyl, $C_3$-$C_7$cycloalkyl, $C_3$-$C_6$alkenyl, benzyl, or phenyl, which phenyl may be optionally substituted with 1, 2 or 3 substituents each independently selected from hydroxy, $C_1$-$C_6$alkoxy, amino, mono- and di$C_1$-$C_6$alkylamino;
or a pharmaceutically acceptable salt or solvate thereof.

In a further aspect, the invention concerns the use of compounds of formula I, as specified herein, for inhibiting HCV. Alternatively, there is provided the use for the manufacture of a medicament of a compound of formula I, as specified herein. The invention also concerns the process for manufacturing compounds of formula I, starting from a the intermediate having the structure depicted above, but wherein $R^4$ is hydrogen.

The group —NH—C($R^8$)($R^{8'}$)—C(=O)— forms an amino acid residue, which includes natural and non-natural amino acid residues. Of particular interest are those amino acid residues wherein $R^8$ is hydrogen. Where in the latter instance $R^{8'}$ is other than hydrogen, the configuration at the asymmetric carbon atom bearing may be that of an L-amino acid. Examples are alanine (Ala), valine (Val), isoleucine (Ile) and phenyl-alanine (Phe) residues, in particular L-Ala, L-Val, L-Ile, and L-Phe. Examples of amino acid residues wherein $R^8$ and $R^{8'}$ together with the carbon atom to which they are attached form $C_3$-$C_7$cycloalkyl, 1,1-cyclopropylamino acid or 1,1-cyclobutylamino acid.

Subgroups of compounds of formula I are those compounds of formula I, or subgroups of compounds of formula I, as defined herein, wherein $R^1$ is hydrogen; or wherein $R^1$ is iodo.

Subgroups of compounds of formula I are those compounds of formula I, or subgroups of compounds of formula I, as defined herein, wherein $R^4$ is a group of formula

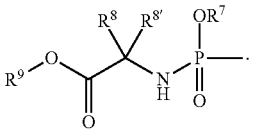

Subgroups of compounds of formula I are those compounds of formula I, or subgroups of compounds of formula I, as defined herein, wherein:
(a) $R^7$ is phenyl, optionally substituted with 1, 2 or 3 substituents each independently selected from halo, $C_1$-$C_6$alkyl, $C_3$-$C_6$alkenyl, $C_1$-$C_6$alkoxy, hydroxy, and amino; or $R^7$ is naphthyl; or $R^7$ is indolyl; or $R^7$ is N-t.butyloxycarbonylindolyl.

(b) $R^7$ is phenyl, optionally substituted with 1, 2 or 3 substituents each independently selected from halo, $C_1$-$C_6$alkyl, $C_3$-$C_6$alkenyl, and $C_1$-$C_6$alkoxy; or $R^7$ is naphthyl;
(c) $R^7$ is phenyl, optionally substituted with halo or $C_1$-$C_6$alkyl, or $R^7$ is naphthyl;
(d) $R^7$ is phenyl, substituted with $C_1$-$C_4$alkyloxycarbonyl;
(e) $R^7$ is phenyl, substituted with $C_1$-$C_2$alkyloxycarbonyl;
(f) $R^7$ is phenyl, optionally substituted with chloro or $C_1$-$C_6$alkyl; or $R^7$ is naphthyl;
(g) $R^7$ is phenyl, optionally substituted with 1, 2 or 3 substituents each independently selected from halo and $C_1$-$C_6$alkyl;
(h) $R^7$ is phenyl, optionally substituted with 1 or 2 substituents each independently selected from halo, $C_1$-$C_6$alkyl, $C_3$-$C_6$alkenyl, $C_1$-$C_6$alkoxy, hydroxy, and amino; or $R^7$ is naphthyl; or $R^7$ is indolyl; or $R^7$ is N-t.butyloxycarbonylindolyl;
(i) $R^7$ is phenyl, optionally substituted with one substituent selected from halo, $C_1$-$C_6$alkyl, $C_3$-$C_6$alkenyl, $C_1$-$C_6$alkoxy, hydroxy, and amino; or $R^7$ is naphthyl; or $R^7$ is indolyl; or $R^7$ is N-t.butyloxycarbonylindolyl;
(j) $R^7$ is phenyl, optionally substituted with one substituent selected from halo, $C_1$-$C_6$alkyl, $C_3$-$C_6$alkenyl, and $C_1$-$C_6$alkoxy;
(k) $R^7$ is naphthyl;
(l) $R^7$ is 5-indolyl or N-t.butyloxycarbonyl-5-indolyl.

In one embodiment, the group $R^7$ being indolyl in the compounds of formula I or any of the subgroups thereof is 5-indolyl or the group $R^7$ being N—$C_1$-$C_6$alkyloxycarbonylindolyl is N-t.butyloxycarbonyl-5-indolyl, in particular N-t.butyloxycarbonyl-5-indolyl. The indolyl group when linked at its 5-position may be represented as follows:

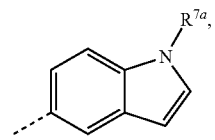

wherein $R^{7a}$ is hydrogen or $C_1$-$C_6$alkyloxy-carbonyl, or in particular $R^{7a}$ is hydrogen or t.butyloxycarbonyl.

Subgroups of compounds of formula I are those compounds of formula I, or subgroups of compounds of formula I, as defined herein, wherein $R^8$ is hydrogen and $R^{8'}$ is methyl or $C_1$-$C_6$alkyl, such as isopropyl or isobutyl. Subgroups of compounds of formula I are those compounds of formula I, or subgroups of compounds of formula I, as defined herein, wherein the

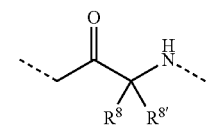

moiety is glycyl, alanyl, or valyl (Gly, Ala, or Val; in particular Gly, L-Ala, or L-Val).

Subgroups of compounds of formula I are those compounds of formula I, or subgroups of compounds of formula I, as defined herein, wherein the

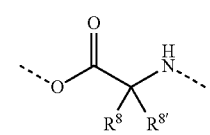

moiety has the structure

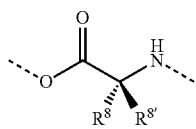

wherein R[8] is hydrogen and R[8'] is hydrogen, $C_1$-$C_6$alkyl, benzyl; or
R[8] is hydrogen and R[8'] is hydrogen or $C_1$-$C_6$alkyl;
R[8] is hydrogen and R[8'] is $C_1$-$C_2$alkyl;
R[8] is hydrogen and R[8'] is methyl.

In one embodiment R[8] and R[8'] together with the carbon atom to which they are attached form $C_3$-$C_7$cycloalkyl; or in particular form $C_3$-$C_4$cycloalkyl; or in particular form cyclopropyl.

Subgroups of compounds of formula I are those compounds of formula I, or subgroups of compounds of formula I, as defined herein, wherein
(a) R[9] is $C_1$-$C_{10}$alkyl, $C_3$-$C_7$cycloalkyl, $C_3$-$C_6$alkenyl, or benzyl;
(b) R[9] is $C_1$-$C_8$alkyl, or benzyl;
(c) R[9] is $C_1$-$C_6$alkyl or benzyl;
(d) R[9] is $C_1$-$C_6$alkyl;
(e) R[9] is $C_1$-$C_4$alkyl; or
(f) R[9] is methyl, ethyl, isopropyl, 1-methyl-propyl, isobutyl, butyl, or t-butyl;
(g) R[9] is benzyl;
(h) R[9] is cyclopentyl; 5-hexenyl; 2,2-dimethyl-butyl; octyl; 2-propyl-pentyl.

Of interest are the compounds mentioned in the experimental part and the pharmaceutically acceptable salts or solvates thereof. Of particular interest are the compound nos. 1, 3, 5, 9, 10, 11, 12, 13, 14, 15 listed in the experimental part.

The compounds of formula I have several centers of chirality, in particular at the carbon atoms 1', 3', and 4'. Although the stereochemistry at these carbon atoms is fixed, the compounds may display at least 75%, preferably at least 90%, such as in excess of 95%, enantiomeric purity at each of the chiral centers.

Chirality may also be present in the substituents, such as where R[4] is

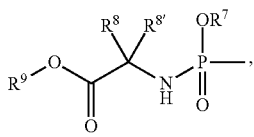

which can have chirality at the R[8] bearing carbon (where R[8] and R[8'] are different) and at the phosphorus atom. The phosphorus center can be present as $R_P$ or $S_P$, or a mixture of such stereoisomers, including racemates. Diastereoisomers resulting from the chiral phosphorus center and a chiral carbon atom may exist as well.

In a further aspect, the invention provides a compound of formula I or a pharmaceutically acceptable salt, hydrate, or solvate thereof, for use in the treatment or prophylaxis (or the manufacture of a medicament for the treatment or prophylaxis) of HCV infection. Representative HCV genotypes in the context of treatment or prophylaxis in accordance with the invention include genotype 1b (prevalent in Europe) or 1a (prevalent in North America). The invention also provides a method for the treatment or prophylaxis of HCV infection, in particular of the genotype 1a or 1b.

The compounds of formula I are represented as a defined stereoisomer. The absolute configuration of such compounds can be determined using art-known methods such as, for example, X-ray diffraction or NMR and/or implication from start materials of known stereochemistry. Pharmaceutical compositions in accordance with the invention will preferably comprise substantially stereoisomerically pure preparations of the indicated stereoisomer.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i e minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography.

The pharmaceutically acceptable addition salts comprise the therapeutically active non-toxic acid and base addition salt forms of the compounds of formula (I). Of interest are the free, i.e. non-salt forms of the compounds of formula I, or of any subgroup of compounds of formula I specified herein.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvates that the compounds of formula I as well as the salts thereof, are able to form. Such solvates are for example hydrates, alcoholates, e.g. ethanolates, propanolates, and the like.

Some of the compounds of formula (I) may also exist in their tautomeric form. For example, tautomeric forms of amide (—C(=O)—NH—) groups are iminoalcohols (—C(OH)=N—), which can become stabilized in rings with aromatic character. The uridine base is an example of such a form. Such forms, although not explicitly indicated in the structural formulae represented herein, are intended to be included within the scope of the present invention.

As used herein "$C_1$-$C_4$alkyl" as a group or part of a group defines saturated straight or branched chain hydrocarbon radicals having from 1 to 4 carbon atoms such as for example methyl, ethyl, 1-propyl, 2-propyl, 1-butyl, 2-butyl, 2-methyl-1-propyl, 2-methyl-2-propyl. "$C_1$-$C_6$alkyl" encompasses $C_1$-$C_4$alkyl radicals and the higher homologues thereof having 5 or 6 carbon atoms such as, for example, 1-pentyl, 2-pentyl, 3-pentyl, 2,2-dimethylpropyl, 1-hexyl, 2-hexyl, 2-methyl-1-butyl, 2-methyl-1-pentyl, 2-ethyl-1-butyl, 3-methyl-2-pentyl, and the like. Of interest amongst $C_1$-$C_6$alkyl is $C_1$-$C_4$alkyl. "$C_1$-$C_{10}$alkyl" encompasses $C_1$-$C_6$alkyl radicals and the higher homologues thereof having 7, 8, 9 or 10 carbon atoms such as, for example, heptyl, 2-heptyl, 3-heptyl, 2-methylhexyl, octyl, 2-octyl, 3-octyl, nonyl, 2-nonyl, 3-nonyl, 2-butylpentyl, decyl, 2-decyl, and the like. Of interest amongst $C_1$-$C_{10}$alkyl is $C_1$-$C_6$alkyl.

'$C_1$-$C_6$alkoxy' means a radical —O—$C_1$-$C_6$alkyl wherein $C_1$-$C_6$alkyl is as defined above. Examples of $C_1$-$C_6$alkoxy are methoxy, ethoxy, n-propoxy, or isopropoxy.

"$C_3$-$C_7$cycloalkyl" includes cyclopropyl, cyclobutyl, cyclopentyl, cyclohexyl, and cycloheptyl. Of interest is cyclopropyl, cyclopentyl and cyclohexyl.

The term "$C_{3-6}$alkenyl" as a group or part of a group defines straight and branched chained hydrocarbon radicals having saturated carbon-carbon bonds and at least one double bond, and having from 3 to 6 carbon atoms, such as, for example, 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. In one embodiment, the carbon atom linking the $C_{3-6}$alkenyl group to the remainder of the molecule is saturated. Of interest amongst $C_{3-6}$alkenyl is $C_{3-4}$alkenyl. Of interest amongst $C_{3-6}$alkenyl or $C_{3-4}$alkenyl are those radicals having one double bond.

The term 'halo' is generic to fluoro, chloro, bromo and iodo.

As used herein, the term '(=O)' or 'oxo' forms a carbonyl moiety when attached to a carbon atom. It should be noted that an atom can only be substituted with an oxo group when the valency of that atom so permits.

The term "monophosphate, diphosphate or triphosphate ester" refers to groups:

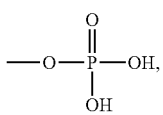 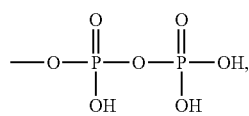

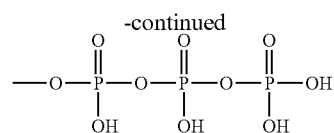

As used herein, the radical positions on any molecular moiety used in the definitions may be anywhere on such a moiety as long as it is chemically stable. When any variable is presentoccurs more than once in any moiety, each definition is independent.

Whenever used herein, the term 'compounds of formula I', or 'the present compounds' or similar terms, it is meant to include the compounds of formula I, including the possible stereochemically isomeric forms, and their pharmaceutically acceptable salts and solvates.

The present invention also includes isotope-labeled compounds of formula I or any subgroup of formula I, wherein one or more of the atoms is replaced by an isotope that differs from the one(s) typically found in nature. Examples of such isotopes include isotopes of hydrogen, such as $^2$H and $^3$H; carbon, such as $^{11}$C, $^{13}$C and $^{14}$C; nitrogen, such as $^{13}$N and $^{15}$N; oxygen, such as $^{15}$O, $^{17}$O and $^{18}$O; phosphorus, such as $^{31}$P and $^{32}$P, sulphur, such as $^{35}$S; fluorine, such as $^{18}$F; chlorine, such as $^{36}$Cl; bromine such as $^{75}$Br, $^{76}$Br, $^{77}$Br and $^{82}$Br; and iodine, such as $^{123}$I, $^{124}$I, $^{125}$I and $^{131}$I. Isotope-labeled compounds of the invention can be prepared by processes analogous to those described herein by using the appropriate isotope-labeled reagents or starting materials, or by art-known techniques. The choice of the isotope included in an isotope-labeled compound depends on the specific application of that compound. For example, for tissue distribution assays, a radioactive isotope such as $^3$H or $^{14}$C is incorporated. For radio-imaging applications, a positron emitting isotope such as $^{11}$C, $^{18}$F, $^{13}$N or $^{15}$O will be useful. The incorporation of deuterium may provide greater metabolic stability, resulting in, e.g. an increased in vivo half life of the compound or reduced dosage requirements.

General Synthetic Methods

The starting material 2'-deoxy-2'-spirocyclopropyluridine can be prepared as described in J. Am, Chem. Soc., 1992, 114, 4007-4008. Compounds of formula I wherein $R^4$ is a group

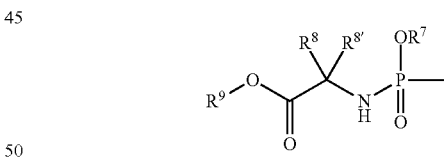

can be prepared by reacting this starting material with a phosphoramidochloridic acid ester 1d. The latter can be prepared by reacting an alcohol 1a with $POCl_3$ in the presence of a base, thus obtaining phosphoryl dichloride 1b, which is further reacted with the amino acid 1c.

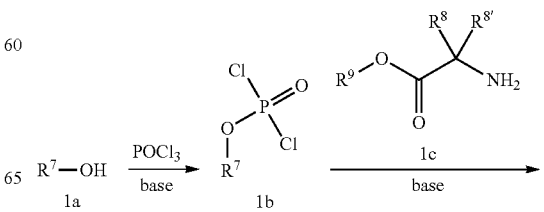

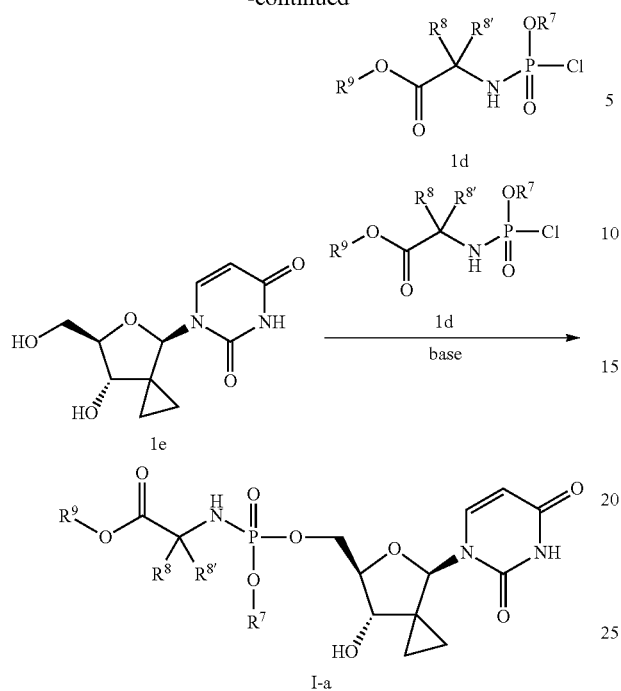

1d

1e

I-a

The compounds of formula I wherein $R^1$ is halo can be prepared by first converting intermediate 1e to its hydroxy-protected form If, which subsequently is halogenated to Ig, for example with N-halo succinimide, e.g. with N-iodo succinimide to Ih. Suitable hydroxy-protecting groups are alkylated silyl groups, in particular sterically hindered alkylated silyl groups such as t.butyldimethylsilyl, triisopropylsilyl, or a 1,1,3,3-tetraisopropyl-disiloxane-1,3-diyl (TIPDS) group. These groups are introduced by reacting the starting alcohols with the appropriate silyl chloride derivative and can be removed afterwards with a fluoride compound such as tetrabutylammonium fluoride (TBAF), yielding compounds Ih. These reactions are represented in the following scheme wherein Pg is a hydroxy-protecting group such as the silyl groups mentioned above.

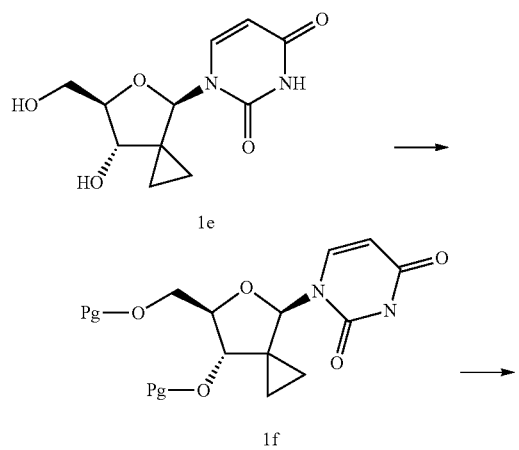

1e

1f

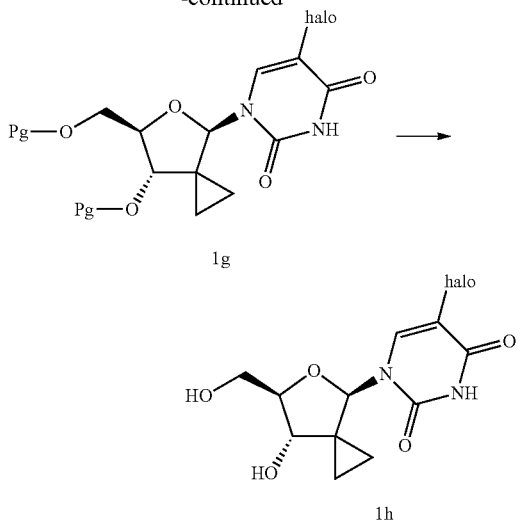

1g

1h

In a further aspect, the present invention concerns a pharmaceutical composition comprising a therapeutically effective amount of a compound of formula I as specified herein, and a pharmaceutically acceptable carrier. A therapeutically effective amount in this context is an amount sufficient to act in a prophylactic way against HCV infection, to stabilize or to reduce HCV infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I show activity against HCV and can be used in the treatment and prophylaxis of HCV infection or diseases associated with HCV. The latter include progressive liver fibrosis, inflammation and necrosis leading to cirrhosis, end-stage liver disease, and HCC. A number of the compounds of this invention moreover are believed to be active against mutated strains of HCV. Additionally, many of the compounds of this invention show a favorable pharmacokinetic profile and have attractive properties in terms of bioavailability, including an acceptable half-life, AUC (area under the curve) and peak values and lacking unfavorable phenomena such as insufficient quick onset and tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula I, including any possible stereoisomers, the pharmaceutically acceptable addition salts or solvates thereof, are useful in the treatment of warm-blooded animals, in particular humans, infected with HCV, and for the prophylaxis of HCV infections. The present invention furthermore relates to a method of treating a warm-blooded animal, in particular human, infected by HCV, or being at risk of infection by HCV, said method comprising the administration of an anti-HCV effective amount of a compound of formula I, as specified herein.

The compounds of the present invention may therefore be used as a medicine, in particular as an anti HCV medicine. Said use as a medicine or method of treatment comprises the systemic administration to HCV infected subjects or to subjects susceptible to HCV infection of an amount effective to combat the conditions associated with HCV infection.

The present invention also relates to the use of the present compounds in the manufacture of a medicament for the treatment or the prevention of HCV infection.

In general it is contemplated that an antiviral effective daily amount would be from about 0.01 to about 700 mg/kg, or about 0.5 to about 400 mg/kg, or about 1 to about 250 mg/kg, or about 2 to about 200 mg/kg, or about 10 to about 150 mg/kg body weight. It may be appropriate to administer the required dose as two, three, four or more sub-doses at appropriate intervals throughout the day. Said sub-doses may be formulated as unit dosage forms, for example, containing about 1 to about 6000 mg, or about 50 to about 5000 mg, or about 100 to about 2000 mg, or about 200 to about 1000 mg, or about 100 to about 600 mg, or about 200 to about 500 mg of active ingredient per unit dosage form.

The invention also relates to a combination of a compound of formula I, a pharmaceutically acceptable salt or solvate thereof, and another antiviral compound, in particular another anti-HCV compound. The term "combination" may relate to a product containing (a) a compound of formula I, as specified above, and (b) optionally another anti-HCV compound, as a combined preparation for simultaneous, separate or sequential use in treatment of HCV infections.

Anti-HCV compounds that can be used in such combinations include HCV polymerase inhibitors, HCV protease inhibitors, inhibitors of other targets in the HCV life cycle, and an immunomodulatory agents, and combinations thereof. HCV polymerase inhibitors include, NM283 (valopicitabine), R803, JTK-109, JTK-003, HCV-371, HCV-086, HCV-796 and R-1479, R-7128, MK-0608, VCH-759, PF-868554, GS9190, XTL-2125, NM-107, GSK625433, R-1626, BILB-1941, ANA-598, IDX-184, IDX-375, MK-3281, MK-1220, ABT-333, PSI-7851, PSI-6130, VCH-916. Inhibitors of HCV proteases (NS2-NS3 inhibitors and NS3-NS4A inhibitors) include BILN-2061, VX-950 (telaprevir), GS-9132 (ACH-806), SCH-503034 (boceprevir), TMC435350 (also referred to as TMC435), TMC493706, ITMN-191, MK-7009, BI-12202, BILN-2065, BI-201335, BMS-605339, R-7227, VX-500, BMS650032, VBY-376, VX-813, SCH-6, PHX-1766, ACH-1625, IDX-136, IDX-316. An example of an HCV NS5A inhibitor is BMS790052, A-831, A-689, NIM-811 and DEBIO-025 are examples of NS5B cyclophilin inhibitors.

Inhibitors of other targets in the HCV life cycle, including NS3 helicase; metallo-protease inhibitors; antisense oligonucleotide inhibitors, such as ISIS-14803 and AVI-4065; siRNA's such as SIRPLEX-140-N; vector-encoded short hairpin RNA (shRNA); DNAzymes; HCV specific ribozymes such as heptazyme, RPI.13919; entry inhibitors such as HepeX-C, HuMax-HepC; alpha glucosidase inhibitors such as celgosivir, UT-231B and the like; KPE-02003002; and BIVN 401.

Immunomodulatory agents include, natural and recombinant interferon isoform compounds, including α-interferon, β-interferon, γ-interferon, and ω-interferon, such as Intron A®, Roferon-A®, Canferon-A300®, Advaferon®, Infergen®, Humoferon®, Sumiferon MP®, Alfaferone®, IFNbeta®, and Feron®; polyethylene glycol derivatized (pegylated) interferon compounds, such as PEG interferon-α-2a (Pegasys®), PEG interferon-α-2b (PEG-Intron®), and pegylated IFN-α-con1; long acting formulations and derivatizations of interferon compounds such as the albumin-fused interferon albuferon α; compounds that stimulate the synthesis of interferon in cells, such as resiquimod; interleukins; compounds that enhance the development of type 1 helper T cell response, such as SCV-07; TOLL-like receptor agonists such as CpG-10101 (actilon), and isatoribine; thymosin α-1; ANA-245; ANA-246; histamine dihydrochloride; propagermanium; tetrachlorodecaoxide; ampligen; IMP-321; KRN-7000; antibodies, such as civacir and XTL-6865; and prophylactic and therapeutic vaccines such as InnoVac C and HCV E1E2/MF59.

Other antiviral agents include, ribavirin, amantadine, viramidine, nitazoxanide; telbivudine; NOV-205; taribavirin; inhibitors of internal ribosome entry; broad-spectrum viral inhibitors, such as IMPDH inhibitors, and mycophenolic acid and derivatives thereof, and including, but not limited to, VX-497 (merimepodib), VX-148, and/or VX-944); or combinations of any of the above.

Particular agents for use in said combinations include interferon-α (IFN-α), pegylated interferon-α or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

In another aspect there are provided combinations of a compound of formula I as specified herein and an anti-HIV compound. The latter preferably are those HIV inhibitors that have a positive effect on drug metabolism and/or pharmacokinetics that improve bioavailabilty. An example of such an HIV inhibitor is ritonavir. As such, this invention further provides a combination comprising (a) a compound of formula I or a pharmaceutically acceptable salt or solvate thereof; and (b) ritonavir or a pharmaceutically acceptable salt thereof. The compound ritonavir, its pharmaceutically acceptable salts, and methods for its preparation are described in WO 94/14436.

The invention also concerns a process for preparing a combination as described herein, comprising the step of combining a compound of formula I, as specified above, and another agent, such as an antiviral, including an anti-HCV or anti-HIV agent, in particular those mentioned above.

The said combinations may find use in the manufacture of a medicament for treating HCV infection in a mammal infected therewith, said combination in particular comprising a compound of formula I, as specified above and interferon-α (IFN-α), pegylated interferon-α, or ribavirin. Or the invention provides a method of treating a mammal, in particular a human, infected with HCV comprising the administration to said mammal of an effective amount of a combination as specified herein. In particular, said treating comprises the systemic administration of the said combination, and an effective amount is such amount that is effective in treating the clinical conditions associated with HCV infection.

In one embodiment the above-mentioned combinations are formulated in the form of a pharmaceutical composition that includes the active ingredients described above and a carrier, as described above. Each of the active ingredients may be formulated separately and the formulations may be co-administered, or one formulation containing both and if desired further active ingredients may be provided. In the former instance, the combinations may also be formulated as a combined preparation for simultaneous, separate or sequential use in HCV therapy. The said composition may take any of the forms described above. In one embodiment, both ingredients are formulated in one dosage form such as a fixed dosage combination. In a particular embodiment, the present invention provides a pharmaceutical composition comprising (a) a therapeutically effective amount of a compound of formula I, including a possible stereoisomeric form thereof, or a pharmaceutically acceptable salt thereof, or a pharmaceutically acceptable solvate thereof, and (b) a therapeutically effective amount of ritonavir or a pharmaceutically acceptable salt thereof, and (c) a carrier.

The individual components of the combinations of the present invention can be administered separately at different times during the course of therapy or concurrently in divided or single combination forms. The present invention is meant to embrace all such regimes of simultaneous or alternating treatment and the term "administering" is to be interpreted accordingly. In a preferred embodiment, the separate dosage forms are administered simultaneously.

In one embodiment, the combinations of the present invention contain an amount of ritonavir, or a pharmaceutically acceptable salt thereof, that is sufficient to clinically improve the bioavailability of the compound of formula I relative to the bioavailability when said compound of formula I is administered alone. Or, the combinations of the present invention contains an amount of ritonavir, or a pharmaceutically acceptable salt thereof, which is sufficient to increase at least one of the pharmacokinetic variables of the compound of formula I selected from $t_{1/2}$, $C_{max}$, $C_{ss}$, AUC at 12 hours, or AUC at 24 hours, relative to said at least one pharmacokinetic variable when the compound of formula I is administered alone.

The combinations of this invention can be administered to humans in dosage ranges specific for each component comprised in said combinations, e.g. the compound of formula I as specified above, and ritonavir or a pharmaceutically acceptable salt, may have dosage levels in the range of 0.02 to 10.0 g/day.

The weight ratio of the compound of formula I to ritonavir may be in the range of from about 30:1 to about 1:15, or about 15:1 to about 1:10, or about 15:1 to about 1:1, or about 10:1 to about 1:1, or about 8:1 to about 1:1, or about 5:1 to about 1:1, or about 3:1 to about 1:1, or about 2:1 to about 1:1. The compound formula I and ritonavir may be co-administered once or twice a day, preferably orally, wherein the amount of the compound of formula I per dose is as described above; and the amount of ritonavir per dose is from 1 to about 2500 mg, or about 50 to about 1500 mg, or about 100 to about 800 mg, or about 100 to about 400 mg, or 40 to about 100 mg of ritonavir.

EXAMPLES

The following examples are meant to illustrate the invention and should not be construed as a limitation of its scope.

In each case, the retention time ($R_t$ (min)) and observed m/z is given. When separation of the two diastereomers was observed in the LC-MS, two retention times are specified. When in a compound no stereochemical indicator is given for the phosphorous atom, that compound is a 1:1 mixture of the two phosphorous-diastereomers. In some cases this mixture was separated but without knowing the exact stereochemical configuration. Such compounds were designated A and B and can be characterized by their physicochemical properties.

Example 1

Synthesis of Compound (1)

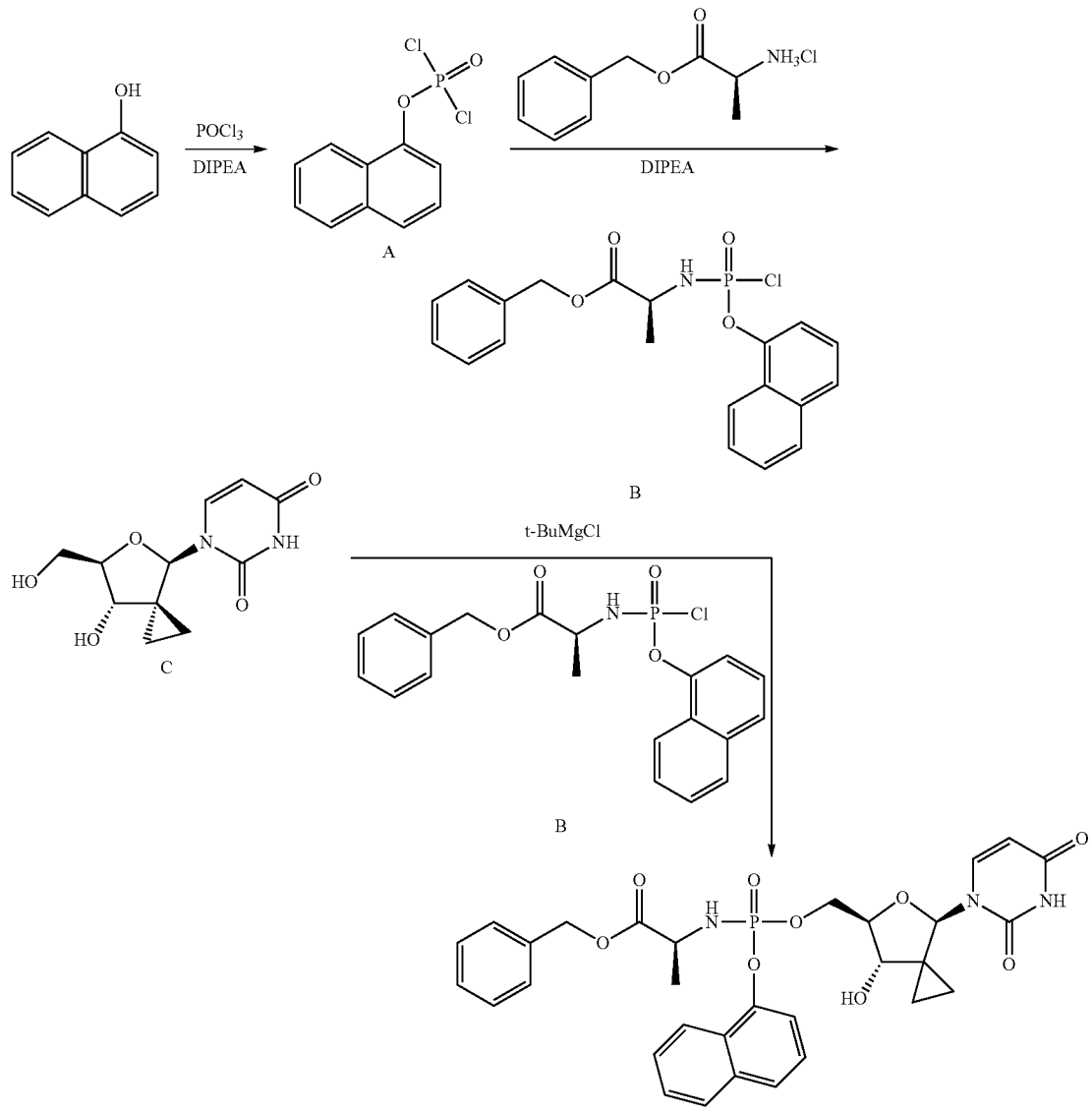

To 1-naphthol (1.0 eq., 69.4 mmol, 10.0 g) in diethylether (250 ml) was added phosphorus oxychloride (1.0 eq., 69.4 mmol, 6.5 ml) and the solution was cooled to −78° C. Dry N,N-diisopropylethylamine (DIPEA; 1.0 eq., 69.4 mmol, 12.1 ml) was added and the resulting solution was left to warm to room temperature overnight. The white slurry was filtered under an inert atmosphere and all volatiles were removed to give A as a colorless liquid that was used without further purification in the next step.

A solution of A (1.0 eq., 4.6 mmol, 1.0 g) and 2-aminopropionic acid benzyl ester hydrochloride (1.0 eq., 4.6 mmol, 1.2 g) in $CH_2Cl_2$ (40 ml) was cooled down to −80° C. Dry DIPEA (2.0 eq., 9.3 mmol, 1.6 ml) was added dropwise. After 1 hour the reaction was warmed up to room temperature. Stirring was continued for 1 more hour and the solvent was removed under reduced pressure. Dry diethylether was added and the precipitate was filtered of and washed twice with dry diethylether under an argon atmosphere. The filtrate was evaporated to dryness to give B which was stored as a 0.97 M solution in tetrahydrofuran (THF) at −18° C.

To a solution of C (1.0 eq., 0.59 mmol, 150 mg) in dry THF (6 ml) was added t-ButylMgCl (1.5 eq., 0.89 mmol, 521 μl, 1.7 M solution in THF) at room temperature. A solution of B (1.4 eq., 0.83 mmol, 852 μl, 0.97 M solution in THF) was added dropwise and the mixture was stirred at room temperature for 2.5 hours. Thirty drops of saturated aqueous $NH_4Cl$ were added and the reaction mixture was evaporated on silica, then purified by column chromatography (0-5% methanol in $CH_2Cl_2$) to give 1 (74 mg, yield=19%, purity=96%) as a mixture of diastereomers. $^1H$ NMR (400 MHz, DMSO-$d_6$) δ ppm 0.39-0.61 (m, 3 H) 1.01-1.12 (m, 1 H) 1.18-1.33 (m, 3 H) 3.88-4.09 (m, 3 H) 4.16-4.31 (m, 1 H) 4.31-4.42 (m, 1 H) 4.96-5.16 (m, 2 H) 5.35-5.49 (m, 2 H) 5.95 (s, 1 H) 6.25-6.37 (m, 1 H) 7.26-7.35 (m, 5 H) 7.36-7.62 (m, 5 H) 7.74 (d, J=8.02 Hz, 1 H) 7.95 (d, J=7.82 Hz, 1 H) 8.11 (t, J=7.92 Hz, 1 H) 11.31 (br. s., 1 H). LC-MS: $R_t$=2.21 min, m/z=620 (M−H)⁻.

The compounds listed hereunder were prepared using a similar procedure as for example 1. Compounds were isolated as a mixture of diastereoisomers. For compound (7), diastereoisomers were isolated and tested separately.

Compound (2)

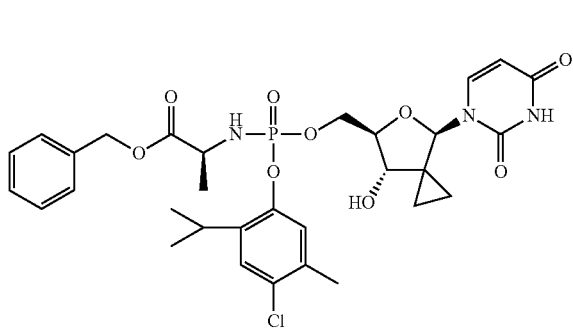 [SMILES: Cc1cc(OP(=O)(N[C@@H](C)C(=O)OCc2ccccc2)OC[C@H]2O[C@@H](n3ccc(=O)[nH]c3=O)C3(CC3)[C@@H]2O)c(C(C)C)cc1Cl]

¹H NMR (400 MHz, DMSO-d₆) δ ppm 0.47-0.62 (m, 3 H) 1.04-1.17 (m, 7 H) 1.24-1.34 (m, 3 H) 2.20 (s, 3 H) 3.12-3.25 (m, 1 H) 3.86-3.98 (m, 2 H) 3.99-4.07 (m, 1 H) 4.09-4.23 (m, 1 H) 4.24-4.35 (m, 1 H) 5.02-5.17 (m, 2 H) 5.36-5.46 (m, 1 H) 5.48-5.57 (m, 1 H) 5.92-5.99 (m, 1 H) 6.16-6.30 (m, 1 H) 7.23-7.39 (m, 7 H) 7.51-7.60 (m, 1 H) 11.31 (br. s., 1 H). LC-MS: $R_t$=2.64 min, m/z=660 (M–H)⁻.

Compound (3)

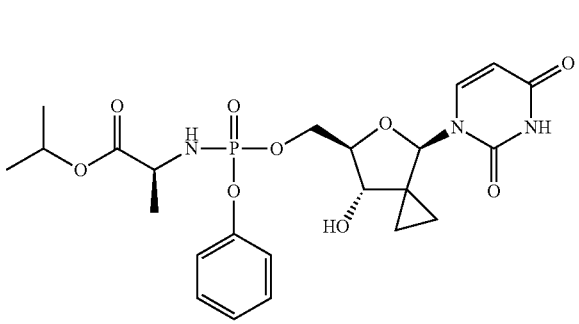 [SMILES: CC(C)OC(=O)[C@H](C)NP(=O)(OC[C@H]1O[C@@H](n2ccc(=O)[nH]c2=O)C2(CC2)[C@@H]1O)Oc1ccccc1]

¹H NMR (400 MHz, DMSO-d₆) δ ppm 0.47-0.62 (m, 3 H) 1.01-1.09 (m, 1 H) 1.14 (d, 6 H) 1.17-1.24 (m, 3 H) 3.67-3.84 (m, 1 H) 3.85-3.96 (m, 1 H) 3.99-4.07 (m, 1 H) 4.09-4.23 (m, 1 H) 4.23-4.35 (m, 1 H) 4.78-4.89 (m, 1 H) 5.34-5.44 (m, 1 H) 5.51-5.59 (m, 1 H) 5.90-5.96 (m, 1 H) 5.96-6.07 (m, 1 H) 7.11-7.25 (m, 3 H) 7.31-7.40 (m, 2 H) 7.52-7.63 (m, 1 H) 11.31 (br. s., 1 H). LC-MS: $R_t$=2.24 min & 2.36 min, m/z=522 (M–H)⁻.

Compound (4)

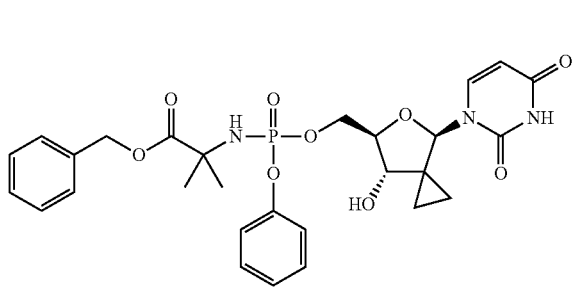 [SMILES: CC(C)(NP(=O)(OC[C@H]1O[C@@H](n2ccc(=O)[nH]c2=O)C2(CC2)[C@@H]1O)Oc1ccccc1)C(=O)OCc1ccccc1]

¹H NMR (400 MHz, DMSO-d₆) δ ppm 0.43-0.63 (m, 3 H) 1.00-1.11 (m, 1 H) 1.31-1.46 (m, 6 H) 3.84-3.92 (m, 1 H) 3.96-4.06 (m, 1 H) 4.09-4.20 (m, 1 H) 4.22-4.32 (m, 1 H) 5.06 (s, 2 H) 5.33-5.43 (m, 1 H) 5.47-5.56 (m, 1 H) 5.88-6.01 (m, 2 H) 7.10-7.23 (m, 3 H) 7.24-7.40 (m, 7 H) 7.46-7.60 (m, 1 H) 11.30 (br. s., 1 H). LC-MS: $R_t$=2.07 min, m/z=584 (M–H)⁻.

Compound (5)

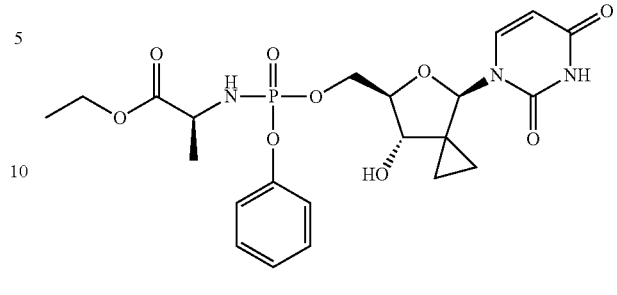

¹H NMR (400 MHz, DMSO-d₆) δ ppm 0.44-0.67 (m, 3 H) 0.99-1.33 (m, 7 H) 3.74-3.97 (m, 2 H) 3.97-4.10 (m, 3 H) 4.10-4.24 (m, 1 H) 4.24-4.39 (m, 1 H) 5.32-5.45 (m, 1 H) 5.51-5.62 (m, 1 H) 5.88-5.98 (m, 1 H) 5.98-6.12 (m, 1 H) 7.11-7.27 (m, 3 H) 7.30-7.44 (m, 2 H) 7.52-7.66 (m, 1 H) 11.31 (br. s., 1 H). LC-MS: $R_t$=2.10 min & 2.23, m/z=508 (M–H)⁻.

Compound (6)

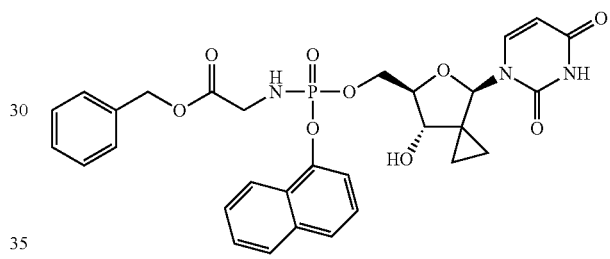

¹H NMR (400 MHz, DMSO-d₆) δ ppm 0.38-0.61 (m, 3 H) 1.01-1.12 (m, 1 H) 3.73-3.86 (m, 2 H) 3.90-3.98 (m, 1 H) 4.00-4.11 (m, 1 H) 4.23-4.33 (m, 1 H) 4.33-4.43 (m, 1 H) 5.09 (s, 2 H) 5.35-5.49 (m, 2 H) 5.96 (s, 1 H) 6.08-6.27 (m, 1 H) 7.22-7.61 (m, 9 H) 7.74 (d, J=7.69 Hz, 1 H) 7.95 (d, J=7.10 Hz, 1 H) 8.12 (d, J=7.72 Hz, 1 H) 11.30 (br. s., 1 H). LC-MS: $R_t$=2.12 min, m/z=606 (M–H)⁻.

Compound (7)

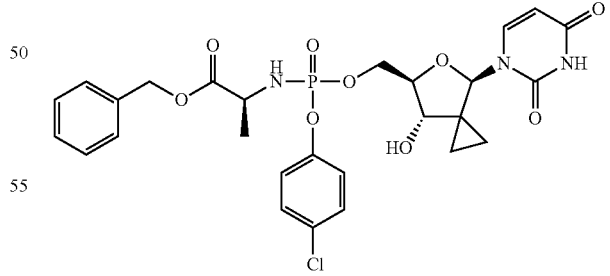

¹H NMR (400 MHz, DMSO-d₆) δ ppm 0.46-0.63 (m, 3 H) 1.01-1.13 (m, 1 H) 1.20-1.31 (m, 3 H) 3.84-3.98 (m, 2 H) 3.99-4.06 (m, 1 H) 4.10-4.23 (m, 1 H) 4.24-4.34 (m, 1 H) 5.02-5.14 (m, 2 H) 5.35-5.44 (m, 1 H) 5.53-5.61 (m, 1 H) 5.90-5.98 (m, 1 H) 6.11-6.24 (m, 1 H) 7.14-7.24 (m, 2 H) 7.28-7.42 (m, 7 H) 7.52-7.61 (m, 1 H) 11.31 (br. s., 1 H). LC-MS: $R_t$=2.98 min & 3.07 min, m/z=604 (M–H)⁻.

Compound (9)

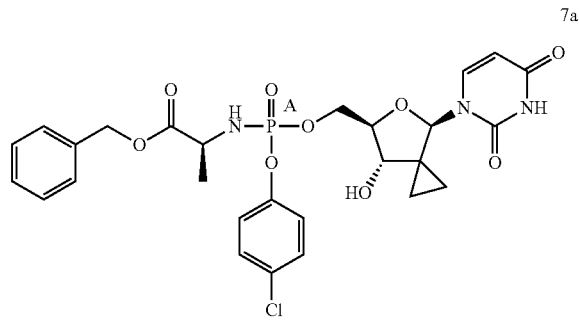

7a

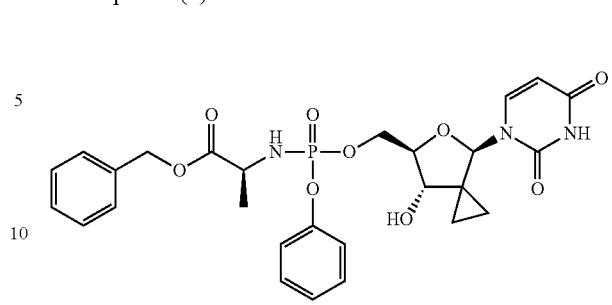

7b

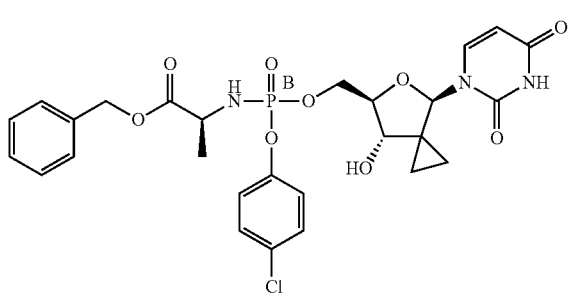 [SMILES: C[C@H](NP(=O)(OC[C@H]1O[C@@H](n2ccc(=O)[nH]c2=O)C2(CC2)[C@@H]1O)Oc1ccc(Cl)cc1)C(=O)OCc1ccccc1]

¹H NMR (400 MHz, DMSO-d₆) δ ppm 0.41-0.64 (m, 3 H) 0.99-1.14 (m, 1 H) 1.16-1.33 (m, 3 H) 3.82-3.97 (m, 2 H) 4.02 (d, J=5.28 Hz, 1 H) 4.08-4.23 (m, 1 H) 4.23-4.34 (m, 1 H) 5.01-5.15 (m, 2 H) 5.34-5.45 (m, 1 H) 5.56 (d, J=8.02 Hz, 1 H) 5.95 (s, 1 H) 6.04-6.17 (m, 1 H) 7.19 (d, J=7.43 Hz, 3 H) 7.26-7.41 (m, 7 H) 7.51-7.62 (m, 1 H) 11.31 (br. s., 1 H). LC-MS: R$_t$=1.98 min., m/z=570 (M−H)⁻.

Compound (10)

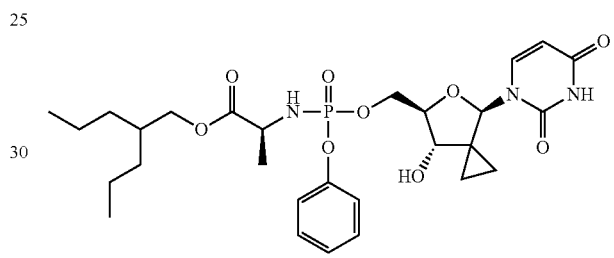

Compound (7a) (Isomer A)

¹H NMR (400 MHz, DMSO-d₆) δ ppm 0.45-0.61 (m, 3 H); 1.01-1.15 (m, 1 H); 1.24 (d, J=6.46 Hz, 3 H); 3.82-3.95 (m, 2 H); 3.96-4.07 (m, 1 H); 4.13-4.24 (m, 1 H); 4.24-4.34 (m, 1 H); 5.09 (s, 2 H); 5.36-5.48 (m, 1 H); 5.58 (d, J=7.63 Hz, 1 H); 5.95 (s, 1 H); 6.20 (t, J=11.35 Hz, 1 H); 7.17 (d, J=7.82 Hz, 2 H); 7.29-7.43 (m, 7 H); 7.55 (d, J=7.63 Hz, 1 H); 11.33 (br. s., 1 H). LC-MS: R$_t$=4.02 min, m/z=604 (M−H)⁻.

Compound (7b) (Isomer B)

¹H NMR (400 MHz, DMSO-d₆) d ppm 1H NMR (400 MHz, DMSO-d₆) d ppm 0.48-0.61 (m, 3 H); 1.02-1.13 (m, 1 H); 1.26 (d, J=7.04 Hz, 3 H); 3.86-3.98 (m, 2 H); 3.99-4.05 (m, 1 H); 4.09-4.20 (m, 1 H); 4.24-4.32 (m, 1 H); 5.03-5.13 (m, 2 H); 5.34-5.44 (m, 1 H); 5.57 (d, J=8.02 Hz, 1 H); 5.94 (s, 1 H); 6.18 (dd, J=12.91, 10.17 Hz, 1 H); 7.21 (d, J=8.61 Hz, 2 H); 7.30-7.41 (m, 7 H); 7.57 (d, J=8.22 Hz, 1 H); 11.32 (br. s., 1 H). LC-MS: Rt=4.07 min, m/z=604 (M−H)⁻.

Compound (8)

¹H NMR (400 MHz, DMSO-d₆) δ ppm 0.43-0.66 (m, 3 H) 0.83 (d, J=5.09 Hz, 6 H) 1.03-1.12 (m, 1 H) 1.12-1.34 (m, 11 H) 1.53-1.66 (m, 1 H) 3.76-4.09 (m, 5 H) 4.10-4.24 (m, 1 H) 4.24-4.36 (m, 1 H) 5.34-5.50 (m, 1 H) 5.56 (d, J=7.63 Hz, 1 H) 5.92-5.98 (m, 1 H) 5.99-6.12 (m, 1 H) 7.14-7.24 (m, 3 H) 7.36 (t, J=7.53 Hz, 2 H) 7.52-7.63 (m, 1 H) 11.32 (br. s., 1 H). LC-MS: R$_t$=2.53 min, m/z=594 (M+H)⁺.

Compound (11)

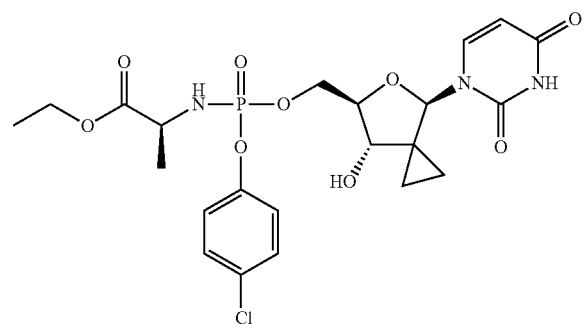 [SMILES: CCOC(=O)[C@H](C)NP(=O)(OC[C@H]1O[C@@H](n2ccc(=O)[nH]c2=O)C2(CC2)[C@@H]1O)Oc1ccc(Cl)cc1]

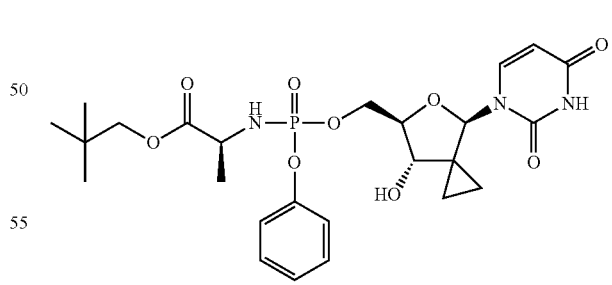

¹H NMR (400 MHz, DMSO-d₆) δ ppm 0.46-0.65 (m, 3 H) 1.02-1.11 (m, 1 H) 1.14 (t, J=7.05 Hz, 3 H) 1.18-1.32 (m, 3 H) 3.73-3.962 (m, 2 H) 3.97-4.09 (m, 3 H) 4.11-4.24 (m, 1 H) 4.24-4.36 (m, 1 H) 5.34-5.46 (m, 1 H) 5.53-5.62 (m, 1 H) 5.90-5.98 (m, 1 H) 6.05-6.18 (m, 1 H) 7.17-7.28 (m, 2 H) 7.43 (d, J=8.80 Hz, 2 H) 7.54-7.62 (m, 1 H) 11.33 (br. s., 1 H). LC-MS: R$_t$=2.41 min & 2.51 min, m/z=542 (M−H)⁻.

¹H NMR (400 MHz, DMSO-d₆) δ ppm 0.43-0.63 (m, 3 H) 0.86 (s, 9 H) 0.99-1.12 (m, 1 H) 1.19-1.32 (m, 3 H) 3.62-3.71 (m, 1 H) 3.72-3.80 (m, 1 H) 3.80-3.97 (m, 2 H) 4.02 (br. s., 1 H) 4.08-4.24 (m, 1 H) 4.24-4.37 (m, 1 H) 5.29-5.46 (m, 1 H) 5.55 (d, J=7.43 Hz, 1 H) 5.94 (d, J=7.24 Hz, 1 H) 6.00-6.13 (m, 1 H) 7.07-7.25 (m, 3 H) 7.35 (t, J=7.73 Hz, 2 H) 7.49-7.66 (m, 1 H) 11.31 (br. s., 1 H). LC-MS: R$_t$=2.08 min, m/z=552 (M+H)⁺.

Compound (12)

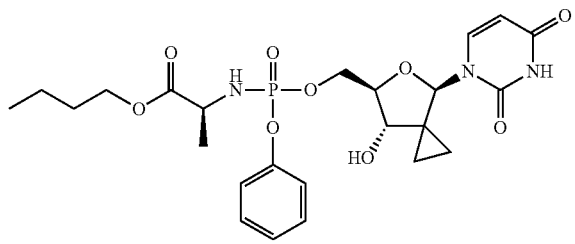 [SMILES: CCCCOC(=O)[C@H](C)NP(=O)(OC[C@H]1O[C@@H](n2ccc(=O)[nH]c2=O)C2(CC2)[C@@H]1O)Oc1ccccc1]

¹H NMR (400 MHz, DMSO-d₆) δ ppm 0.46-0.63 (m, 3 H) 0.81-0.90 (m, 3 H) 1.04-1.12 (m, 1 H) 1.17-1.36 (m, 5 H) 1.45-1.56 (m, 2 H) 3.73-4.09 (m, 5 H) 4.10-4.24 (m, J=11.32, 11.32, 5.66, 5.46 Hz, 1 H) 4.24-4.36 (m, 1 H) 5.33-5.46 (m, 1 H) 5.52-5.60 (m, 1 H) 5.91-5.98 (m, 1 H) 5.98-6.09 (m, 1 H) 7.10-7.28 (m, 3 H) 7.29-7.43 (m, 2 H) 7.51-7.65 (m, 1 H) 11.29 (br. s., 1 H). LC-MS: $R_t$=2.63 min & 2.74, m/z=538 (M+H)⁺.

Compound (13)

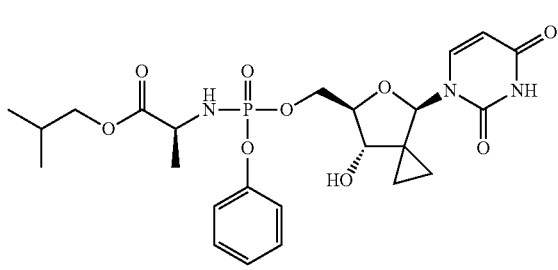 [SMILES: CC(C)COC(=O)[C@H](C)NP(=O)(OC[C@H]1O[C@@H](n2ccc(=O)[nH]c2=O)C2(CC2)[C@@H]1O)Oc1ccccc1]

¹H NMR (400 MHz, CHLOROFORM-d) δ ppm 0.54-0.78 (m, 3 H) 0.85-0.98 (m, 6 H) 1.20-1.33 (m, 1 H) 1.33-1.48 (m, 3 H) 1.84-2.01 (m, J=10.05, 6.68, 3.34, 3.34 Hz, 1 H) 3.64-4.52 (m, 9 H) 5.52-5.78 (m, 1 H) 5.99-6.10 (m, 1 H) 7.14-7.59 (m, 6 H) 8.64 (br. s., 1 H). LC-MS: $R_t$=2.57 min & 2.68 min, m/z=536 (M−H)⁻.

Compound (14)

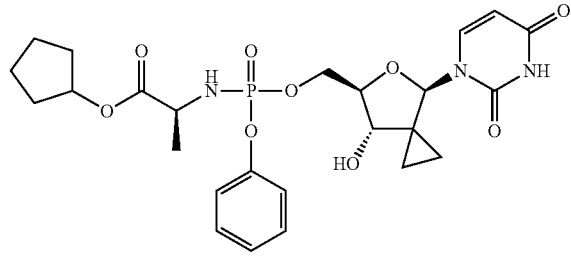 [SMILES: C[C@H](NP(=O)(OC[C@H]1O[C@@H](n2ccc(=O)[nH]c2=O)C2(CC2)[C@@H]1O)Oc1ccccc1)C(=O)OC1CCCC1]

¹H NMR (400 MHz, DMSO-d₆) δ ppm 11.25-11.38 (1 H, m) 7.54-7.63 (1 H, m) 7.32-7.42 (2 H, m) 7.14-7.25 (3 H, m) 5.97-6.06 (1 H, m) 5.92-5.97 (1 H, m) 5.53-5.60 (1 H, m) 5.36-5.44 (1 H, m) 4.98-5.07 (1 H, m) 4.25-4.37 (1 H, m) 4.09-4.25 (1 H, m) 4.00-4.09 (1 H, m) 3.87-3.98 (1 H, m) 3.67-3.84 (1 H, m) 1.70-1.88 (2 H, m) 1.44-1.69 (6 H, m) 1.16-1.27 (3 H, m) 1.02-1.15 (1 H, m) 0.46-0.64 (3 H, m). LC-MS: $R_t$=2.65 min & 2.76 min, m/z=548(M−H)⁻.

Compound (15)

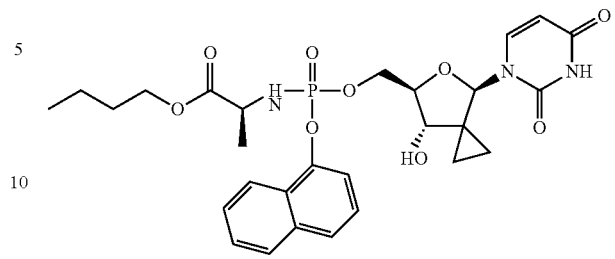

¹H NMR (400 MHz, DMSO-d₆) δ ppm 0.42-0.62 (m, 3 H) 0.74-0.86 (m, 3 H) 1.02-1.10 (m, 1 H) 1.11-1.32 (m, 5 H) 1.34-1.52 (m, 2 H) 3.80-4.01 (m, 4 H) 4.06 (t, J=6.36 Hz, 1 H) 4.16-4.32 (m, 1 H) 4.32-4.42 (m, 1 H) 5.38 (d, J=5.48 Hz, 1 H) 5.40-5.51 (m, 1 H) 5.95 (s, 1 H) 6.14-6.35 (m, 1 H) 7.40-7.63 (m, 5 H) 7.74 (d, J=5.67 Hz, 1 H) 7.95 (d, J=6.06 Hz, 1 H) 8.05-8.18 (m, 1 H) 11.30 (br. s., 1 H). LC-MS: $R_t$=2.19 min, m/z=588 (M+H)⁺.

Compound (16)

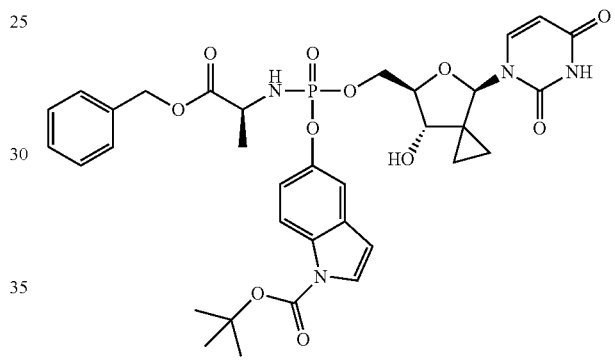

¹H NMR (400 MHz, DMSO-d₆) δ ppm 0.43-0.64 (m, 3 H) 1.02-1.11 (m, 1 H) 1.19-1.30 (m, 3 H) 1.62 (s, 9 H) 3.86-3.99 (m, 2 H) 4.03 (t, J=6.05 Hz, 1 H) 4.11-4.24 (m, 1 H) 4.25-4.35 (m, 1 H) 5.04-5.13 (m, 2 H) 5.33-5.42 (m, 1 H) 5.48-5.56 (m, 1 H) 5.93-5.99 (m, 1 H) 6.00-6.13 (m, 1 H) 6.66 (d, J=2.93 Hz, 1 H) 7.09-7.21 (m, 1 H) 7.23-7.36 (m, 5 H) 7.40-7.47 (m, 1 H) 7.47-7.58 (m, 1 H) 7.69 (d, J=2.93 Hz, 1 H) 7.97 (d, J=8.20 Hz, 1 H) 11.28 (br. s., 1 H). LC-MS: $R_t$=3.54 min & 3.60 min, m/z=711 (M+H)⁺.

Compound (17)

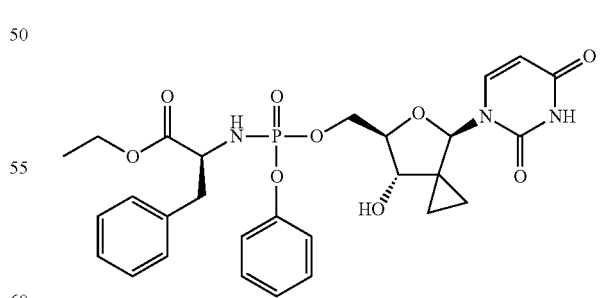

¹H NMR (400 MHz, DMSO-d₆) δ ppm 0.42-0.66 (m, 3 H) 0.95-1.13 (m, 4 H) 2.76-2.87 (m, 1 H) 2.87-3.01 (m, 1 H) 3.76-4.14 (m, 7 H) 5.32-5.43 (m, 1 H) 5.50-5.57 (m, 1 H) 5.91-6.01 (m, 1 H) 6.09-6.27 (m, 1 H) 7.00-7.08 (m, 2 H) 7.11-7.35 (m, 8 H) 7.46-7.56 (m, 1 H) 11.30 (br. s., 1 H). LC-MS: $R_t$=2.69 min & 2.78 min, m/z=586 (M+H)⁺.

Compound (18)

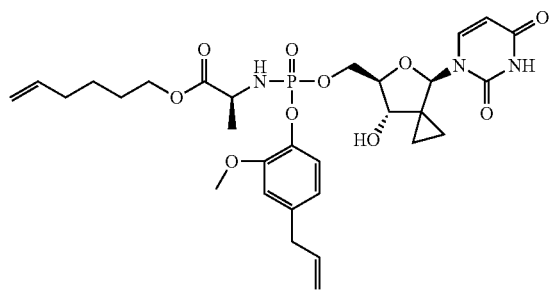 [SMILES: C=CCCCCOC(=O)[C@H](C)NP(=O)(OC[C@H]1O[C@@H](n2ccc(=O)[nH]c2=O)C2(CC2)[C@@H]1O)Oc1ccc(CC=C)cc1OC]

$^1$H NMR (400 MHz, DMSO-d$_6$) δ ppm 0.46-0.63 (m, 3 H) 1.02-1.13 (m, 1 H) 1.17-1.28 (m, 3 H) 1.30-1.43 (m, 2 H) 1.47-1.60 (m, 2 H) 1.94-2.07 (m, 2 H) 3.75 (s, 3 H) 3.79-4.09 (m, 5 H) 4.09-4.24 (m, 1 H) 4.25-4.37 (m, 1 H) 4.88-5.14 (m, 4 H) 5.33-5.44 (m, 1 H) 5.55 (d, J=8.00 Hz, 1 H) 5.67-5.80 (m, 1 H) 5.80-5.90 (m, 1 H) 5.89-6.03 (m, 2 H) 6.64-6.74 (m, 1 H) 6.84-6.94 (m, 1 H) 7.13-7.23 (m, 1 H) 7.54-7.65 (m, 1 H) 11.31 (br. s., 1 H). LC-MS: R$_t$=3.44 min & 3.51 min, m/z=634 (M+H)$^+$.

Compound (19)

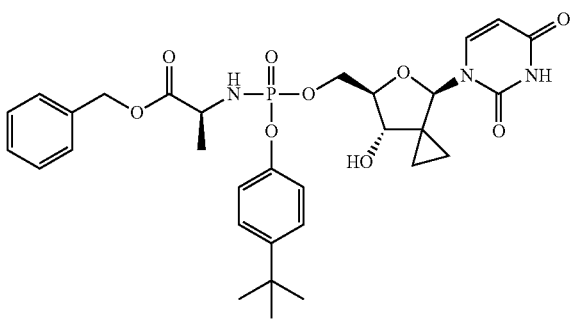 [SMILES: C[C@H](NP(=O)(OC[C@H]1O[C@@H](n2ccc(=O)[nH]c2=O)C2(CC2)[C@@H]1O)Oc1ccc(C(C)(C)C)cc1)C(=O)OCc1ccccc1]

$^1$H NMR (400 MHz, DMSO-d$_6$) δ ppm 0.41-0.62 (m, 3 H) 1.00-1.11 (m, 1 H) 1.23 (s, 12 H) 3.81-3.96 (m, 2 H) 3.96-4.05 (m, 1 H) 4.06-4.20 (m, 1 H) 4.20-4.31 (m, 1 H) 5.00-5.12 (m, 2 H) 5.31-5.42 (m, 1 H) 5.52 (d, J=8.02 Hz, 1 H) 5.93 (s, 1 H) 5.98-6.11 (m, 1 H) 7.00-7.12 (m, 2 H) 7.25-7.38 (m, 7 H) 7.46-7.61 (m, 1 H) 11.29 (br. s., 1 H). LC-MS: R$_t$=2.44 min, m/z=628 (M+H)$^+$.

Compound (20)

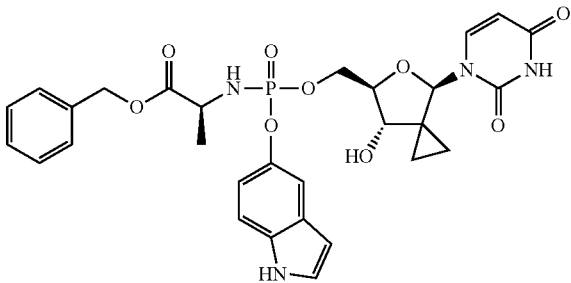 [SMILES: C[C@H](NP(=O)(OC[C@H]1O[C@@H](n2ccc(=O)[nH]c2=O)C2(CC2)[C@@H]1O)Oc1ccc2[nH]ccc2c1)C(=O)OCc1ccccc1]

$^1$H NMR (400 MHz, DMSO-d$_6$) δ ppm 0.40-0.62 (m, 3 H) 1.01-1.10 (m, 1 H) 1.19-1.30 (m, 3 H) 3.84-3.96 (m, 2 H) 3.99-4.06 (m, 1 H) 4.08-4.22 (m, 1 H) 4.22-4.33 (m, 1 H) 5.00-5.12 (m, 2 H) 5.39 (br. s., 1 H) 5.45-5.52 (m, 1 H) 5.91-6.02 (m, 2 H) 6.37 (s, 1 H) 6.92 (t, J=10.37 Hz, 1 H) 7.27-7.41 (m, 8 H) 7.44-7.61 (m, 1 H) 11.12 (br. s., 1 H) 11.29 (br. s., 1 H). LC-MS: R$_t$=1.89 min, m/z=611 (M+H)$^+$.

Compound (21)

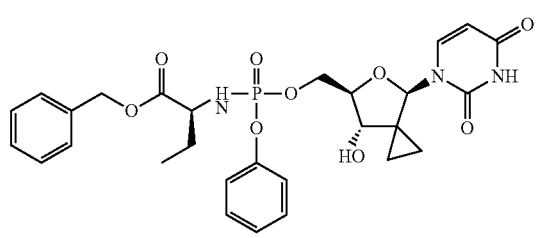 [SMILES: CC[C@H](NP(=O)(OC[C@H]1O[C@@H](n2ccc(=O)[nH]c2=O)C2(CC2)[C@@H]1O)Oc1ccccc1)C(=O)OCc1ccccc1]

$^1$H NMR (400 MHz, DMSO-d$_6$) δ ppm 0.43-0.63 (m, 3 H) 0.71-0.85 (m, 3 H) 1.01-1.14 (m, 1 H) 1.48-1.73 (m, 2 H) 3.64-3.80 (m, 1 H) 3.85-3.97 (m, 1 H) 3.97-4.07 (m, 1 H) 4.07-4.23 (m, 1 H) 4.24-4.34 (m, 1 H) 5.01-5.16 (m, 2 H) 5.32-5.46 (m, 1 H) 5.50-5.60 (m, 1 H) 5.93-5.98 (m, 1 H) 6.00-6.11 (m, 1 H) 7.08-7.24 (m, 3 H) 7.26-7.43 (m, 7 H) 7.50-7.62 (m, 1 H) 11.30 (br. s., 1 H). LC-MS: R$_t$=2.83 min & 2.94 min, m/z=586 (M+H)$^+$.

Compound (22)

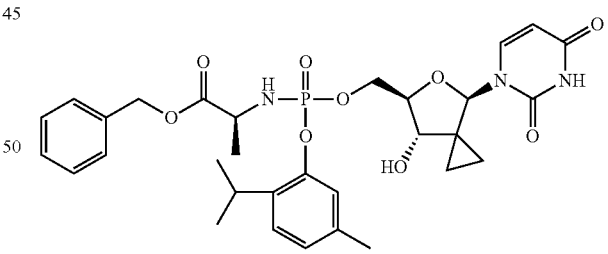

$^1$H NMR (400 MHz, DMSO-d$_6$) δ ppm 0.45-0.63 (m, 3 H) 1.02-1.18 (m, 7 H) 1.29 (d, J=6.06 Hz, 3 H) 2.20 (s, 3 H) 3.12-3.28 (m, 1 H) 3.85-3.98 (m, 2 H) 3.99-4.09 (m, 1 H) 4.09-4.23 (m, 1 H) 4.23-4.34 (m, 1 H) 5.02-5.16 (m, 2 H) 5.35-5.45 (m, 1 H) 5.45-5.55 (m, 1 H) 5.92-6.02 (m, 1 H) 6.08-6.24 (m, 1 H) 6.93 (d, J=7.63 Hz, 1 H) 7.10-7.21 (m, 2 H) 7.34 (br. s., 5 H) 7.50-7.63 (m, 1 H) 11.32 (br. s., 1 H). LC-MS: R$_t$=2.40 min, m/z=628 (M+H)$^+$.

Compound (23)

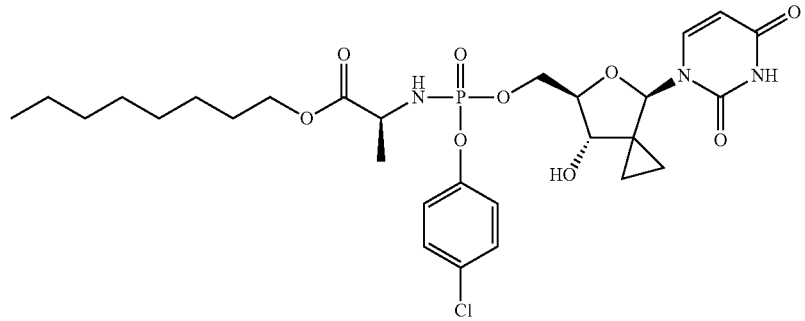 [SMILES: CCCCCCCCOC(=O)[C@H](C)NP(=O)(OC[C@H]1O[C@@H](n2ccc(=O)[nH]c2=O)C2(CC2)[C@@H]1O)Oc1ccc(Cl)cc1]

¹H NMR (400 MHz, DMSO-d₆) δ ppm 0.46-0.63 (m, 3 H) 0.85 (t, J=6.65 Hz, 3 H) 1.04-1.12 (m, 1 H) 1.15-1.32 (m, 13 H) 1.44-1.56 (m, 2 H) 3.73-4.08 (m, 5 H) 4.10-4.24 (m, 1 H) 4.24-4.36 (m, 1 H) 5.35-5.45 (m, 1 H) 5.55-5.63 (m, 1 H) 5.92-5.98 (m, 1 H) 6.05-6.20 (m, 1 H) 7.17-7.27 (m, 2 H) 7.43 (d, J=8.80 Hz, 2 H) 7.55-7.62 (m, 1 H) 11.32 (br. s., 1 H). LC-MS: $R_t$=3.72 min, m/z=626 (M−H)⁺⁻.

Compound (24)

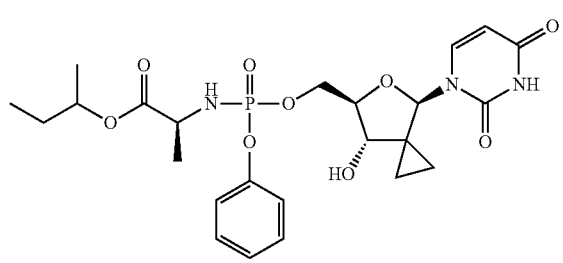 [SMILES: CCC(C)OC(=O)[C@H](C)NP(=O)(OC[C@H]1O[C@@H](n2ccc(=O)[nH]c2=O)C2(CC2)[C@@H]1O)Oc1ccccc1]

¹H NMR (400 MHz, DMSO-d₆) δ ppm 0.46-0.65 (m, 3 H) 0.81 (t, J=7.40 Hz, 3 H) 1.02-1.17 (m, 4 H) 1.17-1.31 (m, 3 H) 1.49 (dq, J=7.28, 7.11 Hz, 2 H) 3.67-3.87 (m, 1 H) 3.87-3.99 (m, 1 H) 3.99-4.10 (m, 1 H) 4.10-4.24 (m, 1 H) 4.24-4.37 (m, 1 H) 4.63-4.81 (m, 1 H) 5.32-5.44 (m, 1 H) 5.50-5.62 (m, 1 H) 5.90-5.97 (m, 1 H) 5.97-6.07 (m, 1 H) 7.12-7.25 (m, 3 H) 7.32-7.41 (m, 2 H) 7.54-7.62 (m, 1 H) 11.30 (s, 1 H). LC-MS: $R_t$=2.58 min & 2.69 min, m/z=536 (M−H)⁻.

Compound (25)

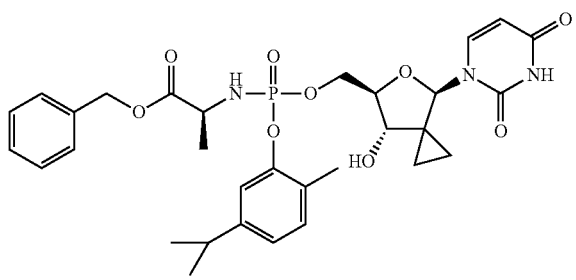 [SMILES: Cc1ccc(C(C)C)cc1OP(=O)(N[C@@H](C)C(=O)OCc1ccccc1)OC[C@H]1O[C@@H](n2ccc(=O)[nH]c2=O)C2(CC2)[C@@H]1O]

¹H NMR (400 MHz, DMSO-d₆) δ ppm 0.45-0.63 (m, 3 H) 1.04-1.09 (m, 1 H) 1.10-1.17 (m, 6 H) 1.22-1.33 (m, 3 H) 2.09-2.21 (m, 3 H) 2.78 (spt, J=6.91 Hz, 1 H) 3.84-3.97 (m, 2 H) 3.98-4.07 (m, 1 H) 4.09-4.24 (m, 1 H) 4.24-4.34 (m, 1 H) 5.03-5.16 (m, 2 H) 5.34-5.45 (m, 1 H) 5.48-5.57 (m, 1 H) 5.92-6.00 (m, 1 H) 6.07-6.17 (m, 1 H) 6.93 (d, J=7.82 Hz, 1 H) 7.12 (d, J=7.82 Hz, 1 H) 7.15 (s, 1 H) 7.27-7.39 (m, 5 H) 7.58 (d, J=8.02 Hz, 1 H) 11.30 (br. s., 1 H). LC-MS: $R_t$=2.44 min, m/z=628 (M+H)⁺.

Compound (26)

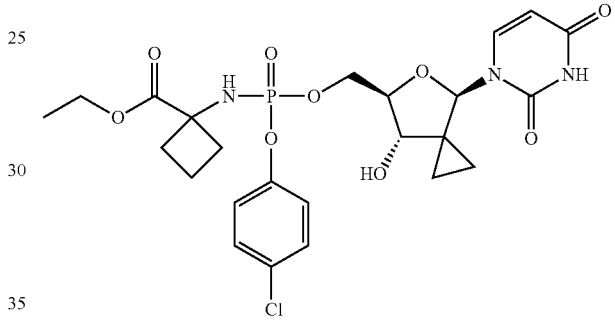

¹H NMR (400 MHz, DMSO-d₆) δ ppm 11.27-11.35 (1 H, m) 7.51-7.64 (1 H, m) 7.39-7.48 (2 H, m) 7.17-7.28 (1 H, m) 6.27-6.38 (1 H, m) 5.90-5.97 (1 H, m) 5.53-5.60 (1 H, m) 5.34-5.42 (1 H, m) 4.26-4.38 (1 H, m) 4.14-4.26 (1 H, m) 3.97-4.12 (3 H, m) 3.85-3.96 (1 H, m) 2.34-2.44 (2 H, m) 2.17-2.28 (1 H, m) 2.05-2.17 (1 H, m) 1.67-1.88 (2 H, m) 1.11-1.19 (3 H, m) 1.04-1.11 (1 H, m) 0.46-0.64 (3 H, m). LC-MS: $R_t$=2.57 min, m/z=568 (M−H)⁻.

Compound (27)

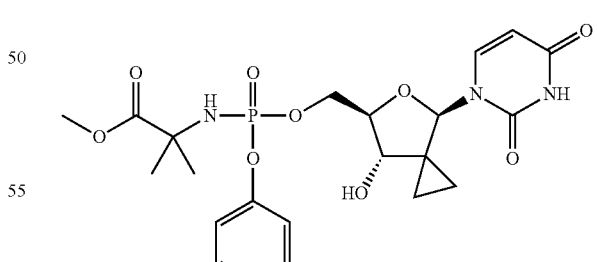

¹H NMR (400 MHz, DMSO-d₆) δ ppm 11.27-11.36 (1 H, m) 7.50-7.65 (1 H, m) 7.30-7.43 (2 H, m) 7.12-7.25 (3 H, m) 5.86-5.98 (2 H, m) 5.50-5.59 (1H, m) 5.36-5.45 (1 H, m) 4.24-4.36 (1 H, m) 4.14-4.24 (1 H, m) 3.98-4.11 (1 H, m) 3.87-3.97 (1 H, m) 3.52-3.60 (3 H, m) 1.28-1.42 (6 H, m) 1.02-1.13 (1 H, m) 0.45-0.64 (3 H, m). LC-MS: $R_t$=1.57 min, m/z=510 (M+H)⁺.

Compound (28)

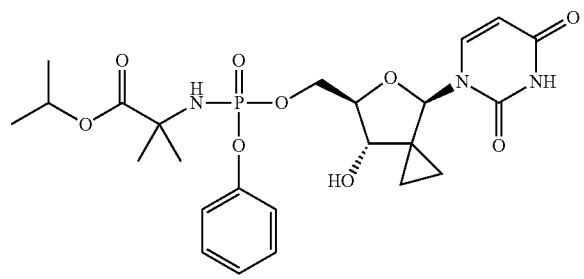 [SMILES: CC(C)OC(=O)C(C)(C)NP(=O)(OC[C@H]1O[C@@H](n2ccc(=O)[nH]c2=O)C2(CC2)[C@@H]1O)Oc1ccccc1]

¹H NMR (400 MHz, DMSO-d$_6$) δ ppm 11.17-11.41 (1 H, m) 7.48-7.64 (1 H, m) 7.30-7.41 (2 H, m) 7.12-7.26 (3 H, m) 5.91-5.96 (1 H, m) 5.74-5.86 (1 H, m) 5.49-5.57 (1 H, m) 5.32-5.41 (1 H, m) 4.77-4.90 (1 H, m) 4.26-4.36 (1 H, m) 4.14-4.25 (1 H, m) 3.99-4.10 (1 H, m) 3.87-3.95 (1 H, m) 1.28-1.41 (6 H, m) 1.11-1.20 (6 H, m) 1.04-1.10 (1 H, m) 0.45-0.63 (3 H, m). LC-MS: R$_t$=2.41 min, m/z=536 (M–H)⁻.

Compound (29)

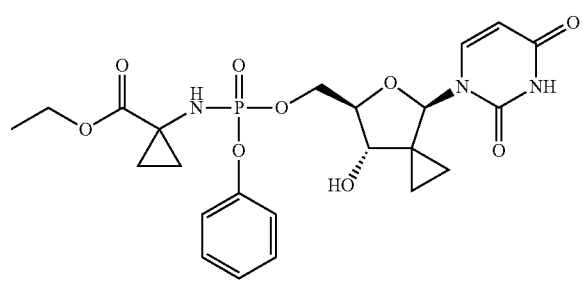 [SMILES: CCOC(=O)C1(NP(=O)(OC[C@H]2O[C@@H](n3ccc(=O)[nH]c3=O)C3(CC3)[C@@H]2O)Oc2ccccc2)CC1]

¹H NMR (400 MHz, DMSO-d$_6$) δ ppm 11.24-11.38 (1 H, m) 7.49-7.65 (1 H, m) 7.29-7.41 (2 H, m) 7.11-7.23 (3 H, m) 6.41-6.56 (1 H, m) 5.90-5.97 (1 H, m) 5.51-5.60 (1 H, m) 5.34-5.44 (1 H, m) 4.26-4.38 (1 H, m) 4.15-4.26 (1 H, m) 3.95-4.08 (3 H, m) 3.87-3.95 (1 H, m) 1.19-1.33 (2 H, m) 1.02-1.17 (5 H, m) 0.92-1.02 (1 H, m) 0.45-0.63 (3 H, m). LC-MS: R$_t$=1.59 min, m/z=522 (M+H)⁺.

Compound (30)

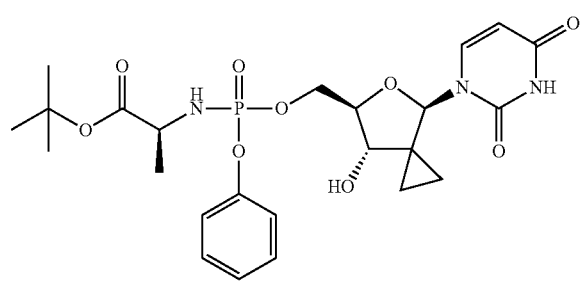 [SMILES: C[C@H](NP(=O)(OC[C@H]1O[C@@H](n2ccc(=O)[nH]c2=O)C2(CC2)[C@@H]1O)Oc1ccccc1)C(=O)OC(C)(C)C]

¹H NMR (400 MHz, DMSO-d$_6$) δ ppm 11.23-11.38 (1 H, m) 7.53-7.64 (1 H, m) 7.29-7.43 (2 H, m) 7.11-7.26 (3 H, m) 5.85-6.01 (2 H, m) 5.50-5.62 (1 H, m) 5.34-5.46 (1 H, m) 4.25-4.38 (1 H, m) 4.09-4.25 (1 H, m) 3.99-4.09 (1 H, m) 3.86-3.98 (1 H, m) 3.59-3.77 (1 H, m) 1.30-1.43 (9 H, m) 1.14-1.28 (3 H, m) 1.00-1.13 (1 H, m) 0.44-0.64 (3 H, m). LC-MS: R$_t$=1.90 min, m/z=538 (M+H)⁺.

Compound (31)

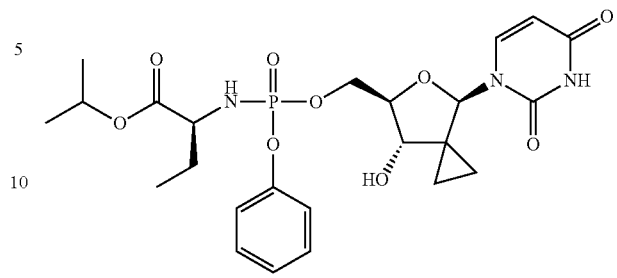

¹H NMR (400 MHz, DMSO-d$_6$) δ ppm 11.19-11.38(1 H, m) 7.52-7.63 (1 H, m) 7.30-7.41 (2 H, m) 7.12-7.24 (3 H, m) 5.90-6.01 (2 H, m) 5.52-5.60 (1 H, m) 5.33-5.43 (1 H, m) 4.79-4.92 (1 H, m) 4.24-4.35 (1 H, m) 4.09-4.24 (1 H, m) 3.99-4.08 (1 H, m) 3.85-3.97 (1 H, m) 3.51-3.67 (1 H, m) 1.45-1.71 (2 H, m) 1.10-1.19 (6 H, m) 1.03-1.10 (1 H, m) 0.75-0.84 (3 H, m) 0.47-0.62 (3 H, m). LC-MS: R$_t$=2.36 min & 2.46 min, m/z=536 (M–H)⁻.

Compound (32)

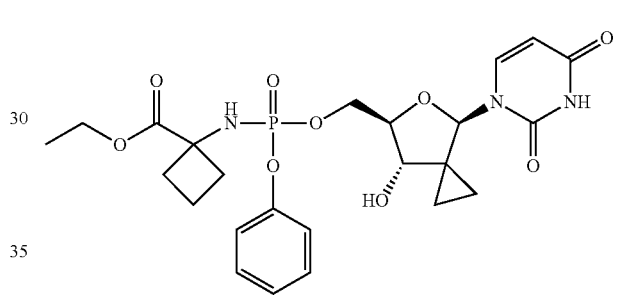

¹H NMR (400 MHz, DMSO-d$_6$) δ ppm 11.21-11.40 (1 H, m) 7.49-7.66 (1 H, m) 7.30-7.43 (2 H, m) 7.12-7.25 (3 H, m) 6.21-6.31 (1 H, m) 5.90-5.98 (1 H, m) 5.50-5.59 (1 H, m) 5.36-5.44 (1 H, m) 4.26-4.37 (1 H, m) 4.15-4.26 (1 H, m) 3.98-4.11 (3 H, m) 3.88-3.97 (1 H, m) 2.32-2.45 (2 H, m) 2.17-2.29 (1 H, m) 2.04-2.18 (1 H, m) 1.67-1.88 (2 H, m) 1.11-1.21 (3 H, m) 1.01-1.11 (1 H, m) 0.45-0.65 (3 H, m). LC-MS: R$_t$=1.76 min, m/z=536 (M+H)⁺.

Compound (33)

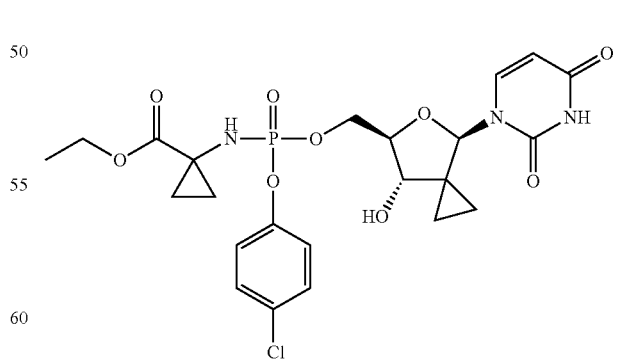

¹H NMR (400 MHz, DMSO-d$_6$) δ ppm 0.45-0.65 (m, 3 H) 0.93-1.04 (m, 1 H) 1.04-1.17 (m, 5 H) 1.21-1.35 (m, 2 H) 3.86-3.95 (m, 1 H) 3.95-4.09 (m, 3 H) 4.16-4.26 (m, 1 H) 4.27-4.38 (m, 1 H) 5.35-5.43 (m,1 H) 5.54-5.62 (m, 1 H) 5.94

(s, 1 H) 6.50-6.64 (m, 1 H) 7.17-7.26 (m, 2 H) 7.38-7.47 (m, 2 H) 7.50-7.63 (m, 1 H) 11.31 (s, 1 H). LC-MS: $R_t$=2.29 min, m/z=554 (M−H)⁻.

Compound (34)

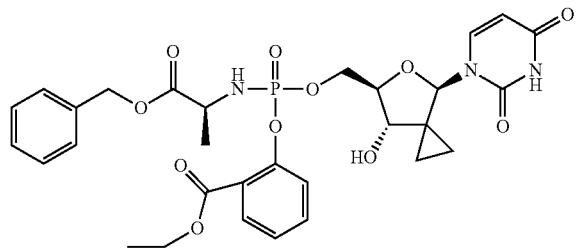 [SMILES: CCOC(=O)c1ccccc1OP(=O)(N[C@@H](C)C(=O)OCc1ccccc1)OC[C@H]1O[C@@H](n2ccc(=O)[nH]c2=O)C2(CC2)[C@@H]1O]

¹H NMR (400 MHz, DMSO-$d_6$) δ ppm 0.44-0.65 (m, 3 H) 1.01-1.13 (m, 1 H) 1.18-1.33 (m, 6 H) 3.84-4.08 (m, 3 H) 4.12-4.37 (m, 4 H) 4.99-5.16 (m, 2 H) 5.31-5.43 (m, 1 H) 5.50-5.61 (m, 1 H) 5.91-6.00 (m, 1 H) 6.00-6.17 (m, 1 H) 7.21-7.40 (m, 6 H) 7.40-7.50 (m, 1 H) 7.50-7.63 (m, 2 H) 7.69-7.83 (m, 1 H) 11.29 (br. s., 1 H). LC-MS: $R_t$=2.96 min, m/z=644 (M+H)⁺.

Example 2

Compound (F), the iodinated analogue of (C) was prepared using the following procedure.

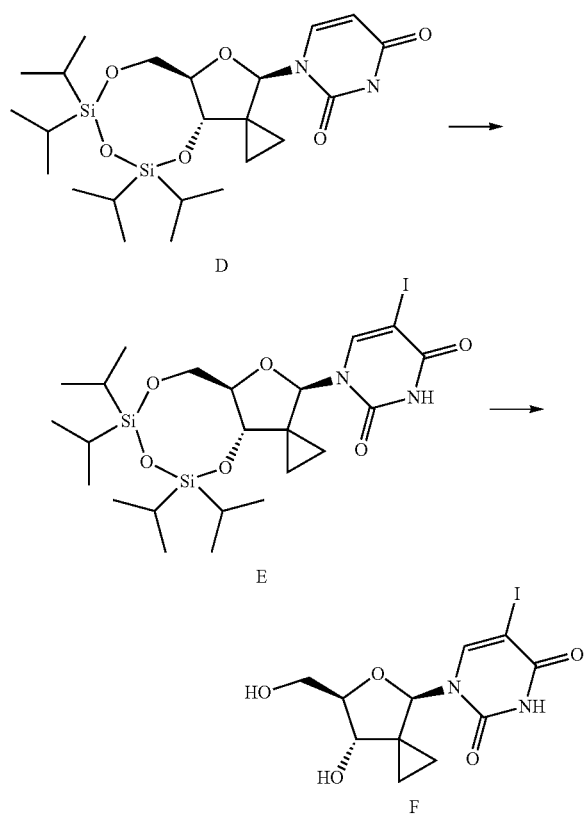

To a solution of (D) (1.44 g, 2.9 mmol) in dry DMF (30 mL) was added at room temperature N-iodosuccinimide (1.63 g, 7.25 mmol, 2.5 eq). The reaction mixture was heated to 110° C. and stirred at that temperature overnight. After cooling to room temperature, the reaction was quenched by the addition of a 7.5% w/v solution of $NaHSO_3$ in saturated $NaHCO_3$ solution. The mixture was further diluted with saturated $NaHCO_3$ solution (250 mL) and extracted with ethyl acetate (3×200 mL). The combined organic layers were dried ($Na_2SO_4$), filtered and concentrated to yield a yellow oil. Purification by column chromatography (heptane/ethyl acetate 10 to 30% gradient) gave (E) as a white solid (1.44 g, 80%). ¹H NMR (400 MHz, DMSO-$d_6$) δ ppm 0.54 (dt, J=10.05, 5.12 Hz, 1 H) 0.62-0.70 (m, 1 H) 0.76 (dt, J=10.05, 5.12 Hz, 1 H) 0.87-1.14 (m, 29 H) 3.74-3.82 (m, 1 H) 3.96 (dd, J=12.88, 2.34 Hz, 1 H) 4.09 (dd, J=12.88, 3.90 Hz, 1 H) 4.53 (d, J=7.80 Hz, 1 H) 5.73 (s, 1 H) 7.89 (s, 1 H) 11.73 (s, 1 H) LC-MS: $R_t$=8.94 min, m/z=645 (M+Na)⁺.

To a suspension of (E) (1.24 g, 1.99 mmol) in methanol (20 mL) was added at room temperature ammonium fluoride (369 mg, 5 eq). The reaction mixture was warmed to 50° C. under argon and stirred for 7 hours. After concentration of the mixture, the obtained residue was purified by column chromatography (dichloromethane/methanol 2.5 to 10% gradient). This yielded (F) as a white solid (711 mg, 92%). ¹H NMR (400 MHz, DMSO-$d_6$) δ ppm 0.50-0.65 (m, 3 H) 1.05 (t, J=5.95 Hz, 1 H) 3.56-3.67 (m, 1 H) 3.70-3.80 (m, 2 H) 4.05-4.15 (m, 1 H) 5.13-5.27 (m, 2 H) 5.85 (s, 1 H) 8.44 (s, 1H) 11.65 (br. s., 1 H) LC-MS: $R_t$=1.32 min, m/z=403 (M+Na)⁺.

Example 3

Synthesis of Phosphoramidates (35-38)

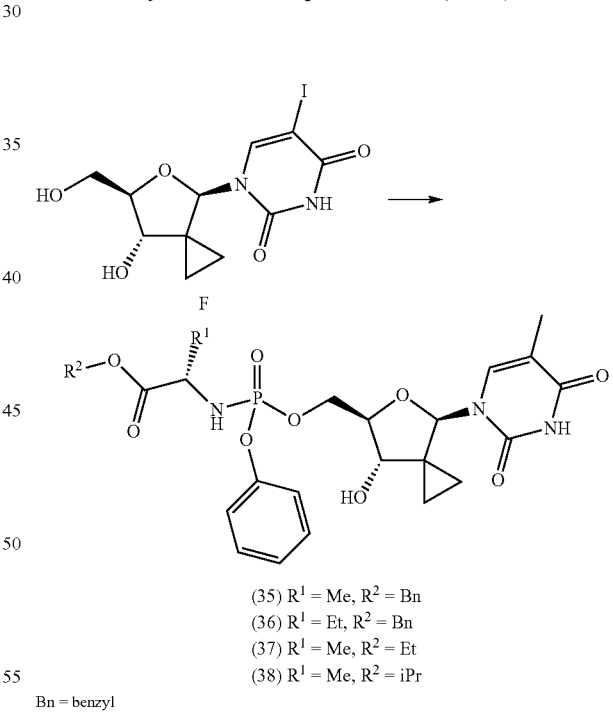

(35) $R^1$ = Me, $R^2$ = Bn
(36) $R^1$ = Et, $R^2$ = Bn
(37) $R^1$ = Me, $R^2$ = Et
(38) $R^1$ = Me, $R^2$ = iPr

Bn = benzyl (F) (120 mg, 0.316 mmol), pre-dried by co-evaporating with pyridine, was dissolved in N-methylimidazole (0.3 mL, 3.79 mmol, 12 eq) and dry dichloromethane (3.2 mL) was added at room temperature under argon a ~1M solution of the appropriate phosphoramidochloridate (1.2 eq). The reaction was stirred for 3 hours. If required extra reagent was added. After full consumption of starting material, the reaction mixture was diluted with dichloromethane and washed with a 0.5M aqueous HCl solution. The aqueous layer was extracted with dichloromethane, and the combined organic layers were dried ($Na_2SO_4$), filtered and concentrated. The residue was purified by column chromatography (dichloromethane/methanol 1 to 10% gradient) to yield the products 36-39 as white solids (yields 68-77%).

Compound (35)

$^1$H NMR (400 MHz, DMSO-$d_6$) δ ppm 0.50-0.62 (m, 3 H) 1.01-1.11 (m, 1 H) 1.19-1.31 (m, 3 H) 3.84-4.00 (m, 2 H) 4.01-4.09 (m, 1 H) 4.11-4.33 (m, 2 H) 5.02-5.14 (m, 2 H) 5.29-5.41 (m, 1 H) 5.83-5.95 (m, 1 H) 6.00-6.14 (m, 1 H) 7.11-7.23 (m, 3 H) 7.26-7.40 (m, 7 H) 7.93 (s, 1 H) 11.69 (br. s., 1 H). LC-MS: $R_t$=5.27 min, m/z=698 $(M+H)^+$.

Compound (36)

$^1$H NMR (400 MHz, DMSO-$d_6$) δ ppm 0.44-0.64 (m, 3 H) 0.70-0.86 (m, 3 H) 1.00-1.12 (m, 1 H) 1.46-1.73 (m, 2 H) 3.67-3.82 (m, 1 H) 3.84-3.98 (m, 1 H) 4.00-4.10 (m, 1 H) 4.10-4.36 (m, 2 H) 4.98-5.15 (m, 2 H) 5.27-5.40 (m, 1 H) 5.83-5.94 (m, 1 H) 5.94-6.07 (m, 1 H) 7.09-7.24 (m, 3 H) 7.26-7.43 (m, 7 H) 7.87-7.99 (m, 1 H) 11.69 (br. s., 1 H). LC-MS: $R_t$=5.58 min, m/z=712 $(M+H)^+$.

Compound (37)

$^1$H NMR (400 MHz, DMSO-$d_6$) δ ppm 0.48-0.64 (m, 3 H) 1.02-1.11 (m, 1 H) 1.14 (t, J=6.93 Hz, 3 H) 1.18-1.30 (m, 3 H) 3.74-3.86 (m, 1 H) 3.86-3.97 (m, 1 H) 3.98-4.10 (m, 3 H) 4.11-4.37 (m, 2 H) 5.27-5.42 (m, 1 H) 5.84-5.92 (m, 1 H) 5.93-6.06 (m, 1 H) 7.11-7.27 (m, 3 H) 7.31-7.42 (m, 2 H) 7.93 (s, 1 H) 11.70 (br. s., 1 H). LC-MS: $R_t$=4.24 min, m/z=653 $(M+NH_4)^+$.

Compound (38)

$^1$H NMR (400 MHz, DMSO-$d_6$) δ ppm 0.49-0.63 (m, 3 H) 1.02-1.10 (m, 1 H) 1.15 (d, J=5.07 Hz, 6 H) 1.18-1.25 (m, 3 H) 3.70-3.84 (m, 1 H) 3.86-3.97 (m, 1 H) 4.02-4.10 (m, 1 H) 4.12-4.34 (m, 2 H) 4.78-4.90 (m, 1 H) 5.29-5.40 (m, 1 H) 5.85-5.91 (m, 1 H) 5.91-5.99 (m, 1 H) 7.12-7.24 (m, 3 H) 7.31-7.40 (m, 2 H) 7.93 (s, 1 H) 11.70 (br. s., 1 H). LC-MS: $R_t$=4.74 min, m/z=667 $(M+NH_4)^+$.

Biological Examples

Replicon Assay

The compounds of formula I were examined for activity in the inhibition of HCV RNA replication in a cellular assay aimed at identifying compounds that inhibit a HCV functional cellular replicating cell line, also known as HCV replicons. The cellular assay was based on a bicistronic expression construct, as described by Lohmann et al. (1999), Science vol. 285 pp. 110-113 with modifications described by Krieger et al. (2001), Journal of Virology 75: 4614-4624, in a multi-target screening strategy.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neoR, neomycine phosphotransferase). The construct is bordered by 5' and 3' NTRs (non-translated regions) from HCV type 1b. Continued culture of the replicon cells in the presence of G418 ($neo^R$) is dependent on the replication of the HCV RNA. The stably transfected replicon cells that express HCV RNA, which replicates autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease the level of detected luciferase activity by 50%, or more specifically, the ability of the genetically linked HCV replicon RNA to replicate.

Cellular Toxicity

Cellular toxicity was determined in the Huh7-CMV-Luc replicon assay. Replicon cells (2500 cells/well), stably transformed with a luciferase reporter gene under control of the cytomegalovirus (CMV) constitutive promotor, were cultured in the presence or absence of test compound concentrations. After three days of incubation at 37° C. in a humidified 5% $CO_2$ atmosphere, cell proliferation was quantified by measuring the Luc activity, and expressed as $CC_{50}$ values (cytotoxicity, 50% inhibitory concentration of cell growth). Tests were performed in 384-well plates.

HIV Assay

Compounds of the invention were tested for their potency against wild type human immunodeficiency virus (HIV). Antiviral activity was evaluated using a cellular assay performed according to the following procedure. The human T-cell line MT4 was engineered with Green Fluorescent Protein (GFP) and a HIV-specific promoter, HIV-1 long terminal repeat (LTR). This cell line, designated MT4 LTR-EGFP, can be used for the in vitro evaluation of anti-HIV activity of investigational compounds. In HIV-1 infected cells, the Tat protein is produced, which upregulates the LTR promotor and eventually leads to stimulation of the GFP reporter production, allowing to measure ongoing HIV-infection fluorometrically. Effective concentration values such as 50% effective concentration (EC50) can be determined and are usually expressed in μM. An EC50 value is defined as the concentration of test compound that reduces the fluorescence of HIV-infected cells by 50%. Monitoring of HIV-1 infection was done using a scanning microscope. Image analysis allows very sensitive detection of viral infection. Measurements were done before cell necrosis, which usually takes place about five days after infection, in particular measurements were performed three days after infection. The column IIIB in the table list the $EC_{50}$ values against the wild type strain IIIB.

The results in Table 1 illustrate that compounds of the present invention show activity against HCV, while lacking activity against HIV. They show favorable results in terms of toxicity and have an acceptable selectivity index (ratio between $EC_{50}$ and $CC_{50}$).

Results

Table 1 shows the replicon results ($EC_{50}$, replicon) and cytotoxicity results ($CC_{50}$ (μM) (Huh-7)) obtained for compounds of the examples given above. Also the HIV activity is given ($EC_{50}$ HIV (μM)) and the cellular toxicity in the HIV cell-line ($CC_{50}$ (μM) (MT-4)).

TABLE 1

| Compound number | $EC_{50}$ (μM) replicon | $CC_{50}$ (μM) (Huh-7) | $EC_{50}$ HIV (μM) | $CC_{50}$ (μM) (MT-4) |
|---|---|---|---|---|
| 1 | 2.8 | >98 | >50 | >32 |
| 2 | 14.3 | >32 | >50 | >32 |

TABLE 1-continued

| Compound number | EC$_{50}$ (μM) replicon | CC$_{50}$ (μM) (Huh-7) | EC$_{50}$ HIV (μM) | CC$_{50}$ (μM) (MT-4) |
| --- | --- | --- | --- | --- |
| 3 | 9.6 | >98 | >98 | >98 |
| 4 | 23.9 | >98 | >98 | >98 |
| 5 | 9.2 | >98 | >90 | >98 |
| 6 | 16.5 | >98 | >90 | >98 |
| 7 | 6.1 | >90 | >90 | >64 |
| 7a | 10.9 | 58.4 | >60 | >50 |
| 7b | 3.4 | >98 | >98 | >90 |
| 8 | 5.9 | >98 | >98 | >98 |
| 9 | 2.9 | >98 | >85 | >98 |
| 10 | 2.8 | >32 | >60 | 29 |
| 11 | 2.8 | >98 | >98 | >98 |
| 12 | 3.1 | >98 | >98 | >98 |
| 13 | 3.2 | >98 | >98 | >98 |
| 14 | 3.3 | >98 | >98 | >98 |
| 15 | 3.6 | >98 | >60 | >60 |
| 16 | 4.2 | >32 | >98 | >32 |
| 17 | 4.4 | >98 | >98 | >98 |
| 18 | 5.1 | >98 | >98 | >64 |
| 19 | 7.2 | >32 | >32 | >32 |
| 20 | 7.6 | >32 | >98 | >98 |
| 21 | 7.8 | >98 | >98 | >80 |
| 22 | 9.2 | >32 | 1.65 | 2.1 |
| 23 | 11.2 | >32 | >98 | >30 |
| 24 | 12.4 | >98 | >98 | >98 |
| 25 | 23.1 | >32 | >98 | 23 |
| 26 | 73.7 | >98 | >98 | >98 |
| 27 | 91.4 | >98 | >98 | >98 |
| 28 | >98 | >98 | >98 | >98 |
| 29 | >98 | >98 | >98 | >98 |
| 30 | >98 | >98 | >98 | >98 |
| 31 | >98 | >98 | >95 | >98 |
| 32 | >98 | >98 | >98 | >98 |
| 33 | >98 | >98 | >98 | >98 |
| 34 | 11.0 | >98 | — | — |

"—" means that the test result is not available

The invention claimed is:

1. A compound of formula I:

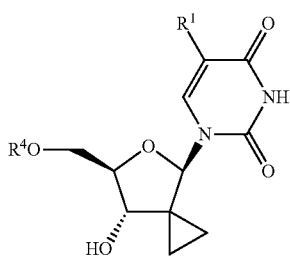

(I)

including any possible stereoisomers thereof, wherein:
R$^1$ is hydrogen or halo;
R$^4$ is a monophosphate, diphosphate or triphosphate ester; or R$^4$ is a group of formula

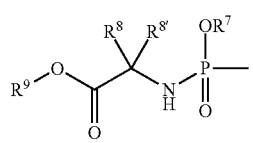

R$^7$ is phenyl, optionally substituted with 1, 2, or with 3 substituents each independently selected from halo, C$_1$-C$_6$alkyl, C$_3$-C$_6$alkenyl, C$_1$-C$_6$alkoxy, C$_1$-C$_6$alkoxycarbonyl, hydroxy, and amino; or R$^7$ is naphthyl; or R$^7$ is indolyl or N-C$_1$-C$_6$alkyloxy-carbon-ylindolyl;
R$^8$ is hydrogen, C$_1$-C$_6$alkyl, benzyl;
R$^{8'}$ is hydrogen, C$_1$-C$_6$alkyl, benzyl; or
R$^8$ and R$^{8'}$ together with the carbon atom to which they are attached form C$_3$-C$_7$cycloalkyl;
R$^9$ is C$_1$-C$_{10}$alkyl, C$_3$-C$_7$cycloalkyl, benzyl, or phenyl, which phenyl may be optionally substituted with 1, 2 or 3 substituents each independently selected from hydroxy, C-C$_6$alkoxy, amino, mono- and diC$_1$-C$_6$alkylamino;
or a pharmaceutically acceptable salt or solvate thereof.

2. The compound according to claim 1, wherein R$^4$ is a group of formula

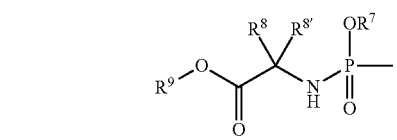

3. The compound according to claim 1, wherein R$^7$ is phenyl, optionally substituted with 1, 2 or 3 substituents each independently selected from halo, C$_1$-C$_6$alkyl, C$_3$-C$_6$alkenyl, and C$_1$-C$_6$alkoxy; or R$^7$ is naphthyl.

4. The compound according to claim 1, wherein R$^7$ is R$^7$ is phenyl, optionally substituted with 1, 2 or 3 substituents each independently selected from halo and C$_1$-C$_6$alkyl.

5. The compound according to claim 1, wherein R$^7$ is phenyl, optionally substituted with halo, or C$_1$-C$_6$alkyl, or R$^7$ is naphthyl.

6. The compound according to of claim 1, wherein R$^8$ is hydrogen, and R$^{8'}$ is hydrogen or C$_1$-C$_6$alkyl.

7. The compound according to claim 1, wherein the

moiety has the structure

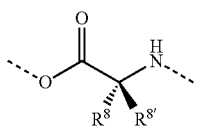

wherein R$^8$ is hydrogen and R$^{8'}$ is hydrogen, C$_1$-C$_6$alkyl, benzyl.

8. The compound according to claim 7, wherein R$^8$ is hydrogen and R$^{8'}$ is C$_1$-C$_2$alkyl.

9. The compound according to claim 7, wherein R$^8$ is hydrogen and R$^{8'}$ is methyl.

10. The compound according to claim 1, wherein R$^9$ is C$_1$-C$_{10}$alkyl, C$_3$-C$_7$cycloalkyl, C$_3$-C$_6$alkenyl, or benzyl.

11. The compound according to claim 10, wherein R$^9$ is C$_1$-C$_8$alkyl, or benzyl.

12. The compound according to claim 10, wherein R$^9$ is methyl, ethyl, isopropyl, 1-methyl-propyl, isobutyl, butyl, t-butyl, benzyl, cyclopentyl, 5-hexenyl, 2,2-dimethyl-butyl, octyl or 2-propyl-pentyl.

13. The compound according to claim 10, wherein $R^9$ is ethyl, isobutyl, butyl, benzyl, cyclopentyl, 5-hexenyl, 2,2-dimethyl-butyl, or 2-propyl-pentyl.

14. A pharmaceutical composition comprising compound of formula I of claim 1 and a pharmaceutically acceptable carrier.

15. The method of treating a HCV infection comprising administrating an anti-HCV effective amount of a compound according to claim 1 to a patient in need of such treatment.

* * * * *